United States Patent
Starzl

(10) Patent No.: US 10,611,828 B2
(45) Date of Patent: *Apr. 7, 2020

(54) COMPOSITIONS AND METHODS FOR TREATMENT IN BROAD-SPECTRUM, UNDIFFERENTIATED OR MIXED CLINICAL APPLICATIONS

(71) Applicant: PANTHERYX, INC., Boulder, CO (US)

(72) Inventor: Timothy W. Starzl, Boulder, CO (US)

(73) Assignee: PANTHERYX, INC., Boulder, CO (US)

( * ) Notice: Subject to any disclaimer, the term of this patent is extended or adjusted under 35 U.S.C. 154(b) by 219 days.

This patent is subject to a terminal disclaimer.

(21) Appl. No.: 15/616,724

(22) Filed: Jun. 7, 2017

(65) Prior Publication Data

US 2017/0327564 A1 Nov. 16, 2017

Related U.S. Application Data

(63) Continuation of application No. 13/302,836, filed on Nov. 22, 2011, now Pat. No. 9,701,735.

(60) Provisional application No. 61/416,667, filed on Nov. 23, 2010.

(51) Int. Cl.
| | | |
|---|---|---|
| *C07K 16/10* | (2006.01) | |
| *C07K 16/12* | (2006.01) | |
| *A61K 39/00* | (2006.01) | |

(52) U.S. Cl.
CPC ............ *C07K 16/10* (2013.01); *C07K 16/121* (2013.01); *C07K 16/1232* (2013.01); *C07K 16/1282* (2013.01); *A61K 2039/507* (2013.01); *A61K 2039/545* (2013.01); *A61K 2039/70* (2013.01); *C07K 2317/11* (2013.01)

(58) Field of Classification Search
None
See application file for complete search history.

(56) References Cited

U.S. PATENT DOCUMENTS

| | | |
|---|---|---|
| 4,341,763 A | 7/1982 | Zygraich |
| 4,376,110 A | 3/1983 | David et al. |
| 4,377,569 A | 3/1983 | Plymate |
| 4,550,019 A | 10/1985 | Polson |
| 4,748,018 A * | 5/1988 | Stolle ............ C07K 16/02 424/157.1 |
| 4,816,563 A | 3/1989 | Wilson et al. |
| 4,816,567 A | 3/1989 | Cabilly et al. |
| 5,017,372 A | 5/1991 | Hastings |
| 5,080,895 A | 1/1992 | Tokoro |
| 5,198,213 A | 3/1993 | Stott et al. |
| 5,260,057 A | 11/1993 | Cordle et al. |
| 5,367,054 A | 11/1994 | Lee |
| 5,470,835 A | 11/1995 | Kirkpatrick et al. |
| 5,554,372 A | 9/1996 | Hunter |
| 5,585,098 A | 12/1996 | Coleman |
| 5,719,267 A | 2/1998 | Carroll et al. |
| 5,753,228 A | 5/1998 | Sterling et al. |
| 5,762,934 A | 6/1998 | Williams et al. |
| 5,840,700 A | 11/1998 | Kirkpatrick et al. |
| 5,846,569 A | 12/1998 | Anderson et al. |
| 5,876,735 A | 3/1999 | Reed |
| 6,348,223 B1 | 2/2002 | Claycamp et al. |
| 6,348,230 B1 | 2/2002 | Campbell et al. |
| 6,410,058 B2 | 6/2002 | Gohlke et al. |
| 6,419,926 B2 | 7/2002 | Kodama et al. |
| 6,468,534 B1 | 10/2002 | Hennen et al. |
| 6,475,511 B2 | 11/2002 | Gohlke et al. |
| 6,521,277 B1 | 2/2003 | Mortensen |
| 6,537,550 B1 | 3/2003 | Larsson et al. |
| 6,569,447 B2 | 5/2003 | Kisic et al. |
| 6,793,921 B2 | 9/2004 | Kodama et al. |
| 6,866,868 B1 | 3/2005 | Lisonbee et al. |
| 6,939,954 B2 | 9/2005 | Yoder et al. |
| 7,445,782 B2 | 11/2008 | Fairbrother et al. |
| 7,575,698 B2 | 8/2009 | Abe et al. |
| 7,713,527 B2 | 5/2010 | Pradip et al. |
| 7,727,531 B2 | 6/2010 | Fairbrother et al. |
| 7,815,943 B2 | 10/2010 | Hennen |
| 7,862,799 B2 | 1/2011 | Tay et al. |
| 2001/0009668 A1 | 7/2001 | Richardson |
| 2001/0021384 A1 | 9/2001 | Jourdier et al. |
| 2002/0044942 A1 | 4/2002 | Dopson |
| 2002/0143157 A1 | 10/2002 | Yoder et al. |
| 2003/0021778 A1 | 1/2003 | Simon |
| 2003/0103989 A1 | 6/2003 | Hodgkinson et al. |
| 2003/0185856 A1 | 10/2003 | Lee et al. |
| 2005/0058716 A1 | 3/2005 | Lisonbee et al. |
| 2006/0134101 A1 | 6/2006 | Larsson et al. |
| 2006/0233781 A1 | 10/2006 | Pedersen et al. |
| 2007/0053917 A1 | 3/2007 | Robins-Browne et al. |
| 2007/0053919 A1 | 3/2007 | Lisonbee et al. |
| 2007/0264264 A1 | 11/2007 | Evans et al. |
| 2007/0274983 A1 | 11/2007 | Kluijtmans et al. |
| 2008/0031903 A1 | 2/2008 | Gambotto et al. |
| 2008/0069813 A1 | 3/2008 | Yoder et al. |
| 2008/0081076 A1 | 4/2008 | Lisonbee et al. |
| 2008/0124321 A1 | 5/2008 | Yoder et al. |
| 2008/0138435 A1 | 6/2008 | Van Den Berg et al. |
| 2008/0206233 A1 | 8/2008 | Frenken et al. |
| 2008/0274945 A1 | 11/2008 | Van Laere et al. |

(Continued)

FOREIGN PATENT DOCUMENTS

| | | |
|---|---|---|
| CN | 1037276 | 11/1989 |
| CN | 1642561 | 7/2005 |

(Continued)

OTHER PUBLICATIONS

Yokoyama et al. Infection and Immunity 1992 vol. 60, pp. 998-1007 (Year: 1992).*

(Continued)

*Primary Examiner* — Shanon A. Foley
*Assistant Examiner* — Myron G Hill
(74) *Attorney, Agent, or Firm* — Merchant & Gould P.C.

(57) ABSTRACT

The disclosure provides improved compositions and methods for passive immunization. In embodiments, a composition comprising a synergistic combination of specific polyclonal antibodies in a carrier matrix is provided. The disclosure provides effective, economical compositions and methods for the treatment of diarrhea and enteric infections in broad-spectrum, undifferentiated, or mixed clinical applications.

50 Claims, 9 Drawing Sheets

(56) References Cited

U.S. PATENT DOCUMENTS

Figure 1:
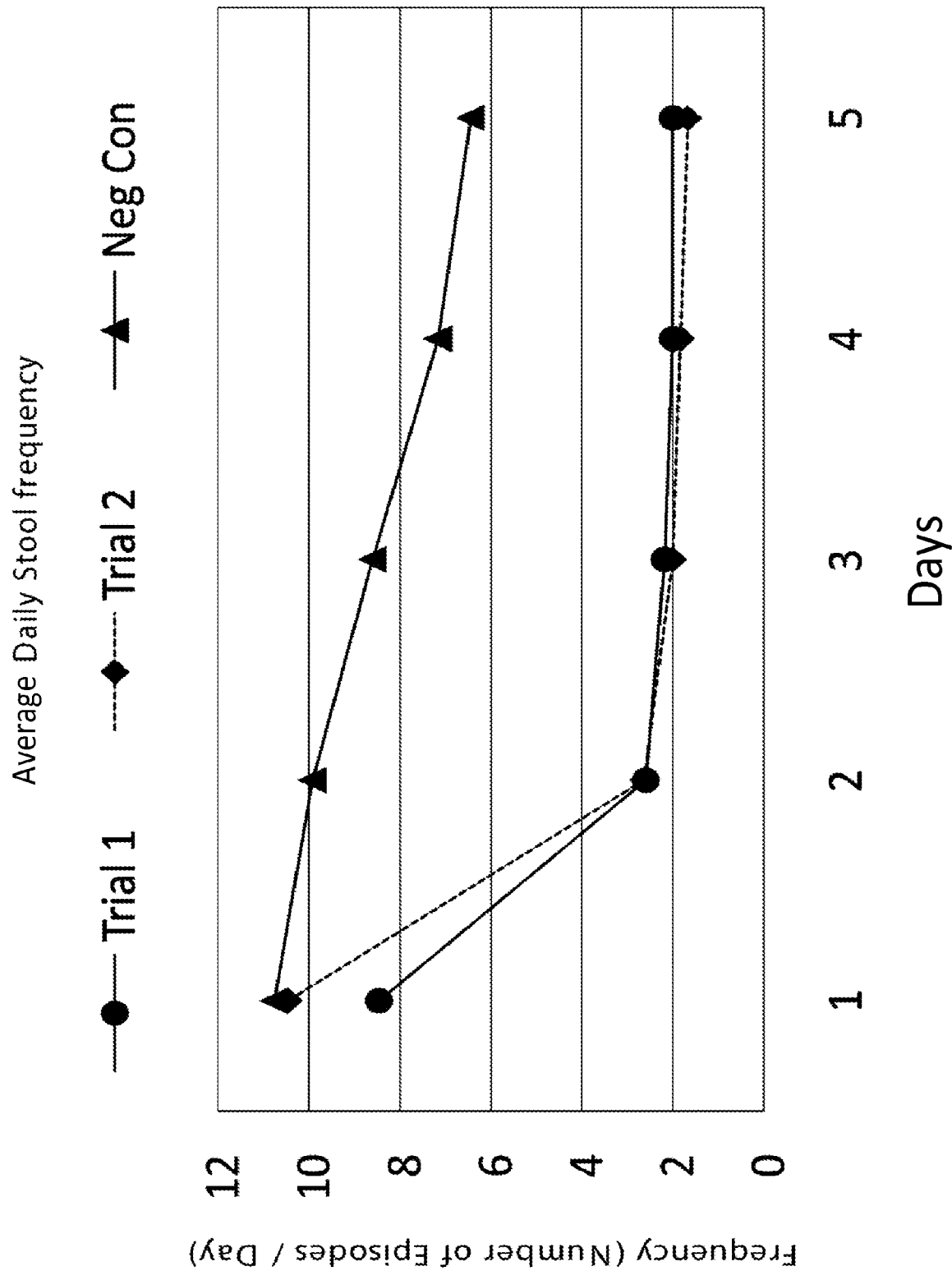

| | | |
|---|---|---|
| 2009/0053197 A1 | 2/2009 | Ramaekers |
| 2009/0092621 A1 | 4/2009 | Fairbrother et al. |
| 2009/0142377 A1 | 6/2009 | Gebbink et al. |
| 2009/0226418 A1 | 9/2009 | Frenken et al. |
| 2009/0246207 A1 | 10/2009 | Rahmani |
| 2009/0311333 A1 | 12/2009 | Elfstrand et al. |
| 2009/0317421 A1 | 12/2009 | Missiakas et al. |
| 2009/0324723 A1 | 12/2009 | Rawlin et al. |
| 2010/0183627 A1 | 7/2010 | Fairbrother et al. |
| 2010/0183632 A1 | 7/2010 | Fox |
| 2010/0233162 A1 | 9/2010 | Larsson et al. |
| 2010/0266607 A1 | 10/2010 | Fox |
| 2010/0297140 A1 | 11/2010 | Scammell |
| 2011/0129479 A1 | 6/2011 | Tobin |
| 2011/0200610 A1 | 8/2011 | Ilan et al. |

FOREIGN PATENT DOCUMENTS

| | | |
|---|---|---|
| EP | 0074240 | 3/1983 |
| EP | 0152270 | 8/1985 |
| EP | 0914831 | 12/1999 |
| JP | 60-123428 | 7/1985 |
| JP | H10-265393 | 10/1998 |
| WO | 89/10139 | 11/1989 |
| WO | 98/014209 | 4/1998 |
| WO | 1999/004804 | 2/1999 |
| WO | 2003/080082 | 10/2003 |
| WO | 2004/078209 | 9/2004 |
| WO | 2009/127519 | 10/2009 |
| WO | 2010/044095 | 4/2010 |
| WO | 2010/125565 | 11/2010 |
| WO | 2011/017483 | 2/2011 |

OTHER PUBLICATIONS

Ikemori et al. (Vet Microb. 1997 vol. 58 pp. 105-111 (Year: 1997).*
Sarker et al. Pediatric Infectious Dis J, vol. 17, pp. 1149-1154 (Year: 1998).*
Alder et al., "Diversity and Function of Adaptive Immune Receptors in a Jawless Vertebrate," Science, 310:1970-1973, (Dec. 23, 2005).
Bahl et al. "Efficacy of zinc-fortified oral rehydration solution in 6- to 35-month-old children with acute diarrhea," The Journal of Pediatrics, 141(5):677-682 (Nov. 2002).
Berge et al., "Evaluation of the effects of oral colostrum supplementation during the first fourteen days on the health and performance of preweaned calves," Journal of Dairy Science, 2009, vol. 92, pp. 286-295.
Bhutta et al., "Therapeutic effects of oral zinc in acute and persistent diarrhea in children in developing countries: pooled analysis of randomized controlled trials [1-3]," The American Journal of Clinical Nutrition, 72:1516-1522, (2000).
Black et al., "Maternal and child undernutrition: global and regional exposures and health consequences", The Lancet, 371(9608):243-260 (2008).
Brandtzaeg "Mucosal immunity in the female genital tract[1]," Journal of Reproductive Immunology 36:23-50 (Sep. 2, 1997).
Brandtzaeg "Mucosal immunity in infectious disease and allergy," International Congress Series, 1257:11-20 (Aug. 25, 2003).
Brandtzaeg "Induction of secretory immunity and memory at mucosal surfaces," Vaccine, 25:5467-5484 (2007).
Brussow et al., "Bovine Milk Immunoglobulins for Passive Immunity to Infantile Rotavirus Gastroenteritis", J Clin Microbiol, 25(6):982-986 (Jun. 1987).
Casswall et al. Treatment of enterotoxigenic and enteropathogenic *Escherichia coli*-induced diarrhoea in children with bovine immunoglobulin milk concentrate from hyperimmunized cows: a double-blind, placebo-controlled, clinical trial, Scandinavian Journal of Gastroenterology, 35(7):711-718 (Jul. 2000).
Chilean Examination Report dated Oct. 13, 2014 for related Chilean Patent Application Serial No. 1469-2013.
Chinese Office Action and Search Report dated May 7, 2014 for related Chinese Patent Application Serial No. 201180065699.4; English Translation.
Chinese Office Action and Search Report dated Jun. 16, 2017 for related Chinese Patent Application Serial No. 201510309672.5; English Translation.
Clackson et al., "Making antibody fragments using phage display libraries," Nature, 352:624-628 (Aug. 15, 1991).
Columbian Office Action dated Sep. 12, 2014 for related Columbian Patent Application Serial No. 13-148.236. With English Translation.
Crabb "Antibody-based Immunotherapy of Cryptosporidiosis," Advances in Parasitology, 40:122-149.
Da Silva et al., "IgY: A promising antibody for use in immunodiagnostic and in immunotherapy", Veterinary Immunol. Immunopath., 135:73-180 (2010).
Dean, "Hyperimmune Eggs Capture Natural Immune Support," Alternative & Complementary Therapies, pp. 118-124 (Jun. 2000).
Davidson et al., "Passive immunisation of children with bovine colostrum containing antibodies to human rotavirus", The Lancet, 2(8665):709-712 (Sep. 23, 1989).
Dorland, Definition of "hyperimmunization"; Dorland's Illustrated Medical Dictionary 32nd Edition, Elsevier Saunders,Philadelphia, PA; p. 890 (2012).
Enos et al., "Probiotics and nutrients for the first 1000 days of life in the developing world", Beneficial Microbes, 4(1):3-16 (Mar. 1, 2013).
Eurasian Office Action dated Apr. 9, 2015, with English Translation.
Gaffey et al., "Dietary management of childhood diarrhea in low- and middle-income countries: a systematic review", BMC Public Health, 13(Suppl 3):S17:1-16 (2013).
Guarino et al., "The management of acute diarrhea in children in developed and developing areas: from evidence base to clinical practice", Expert Opinion on Pharmacotherapy, 13(1):17-26 (Jan. 2012).
Hamal et al., "Maternal Antibody Transfer from Dams to Their Egg Yolks, Egg Whites, and Chicks in Meat Lines of Chickens," Poultry Science Association, Inc., pp. 1364-1372 (2006).
Hassl et al., "Purification of egg yolk immunoglobulins A two-step procedure using hydrophobic interaction chromatography and gel filtration," Journal of Immunological Methods, 110:225-228 (Jan. 18, 1988).
Hatta et al., "A Novel Isolation Method for Hen Egg Yolk Antibody, "IgY"," Agric. Biol. Chem., 54(10):2531-2535 (Feb. 5, 1990).
Hau et al., "Refinement of Polyclonal Antibody Production by Combining Oral Immunization of Chickens with Harvest of Antibodies from the Egg Yolk", ILAR Journal, vol. 46, No. 3, pp. 294-299 (2005).
Hilpert et al., "Use of bovine milk concentrate containing antibody to rotavirus to treat rotavirus gastroenteritis in infants", The Journal of Infectious Diseases, 156(1):158-166 (Jul. 1987).
Huppertz et al., "Bovine colostrum ameliorates diarrhea in infection with diarrheagenic *Escherichia coli*, shiga toxin-producing *E. coli*, and *E. coli* expressing intimin and hemolysin" J Pediatr Gastroenterol Nutr., 29(4):452-456 (Oct. 1999).
Ikemori et al., "Passive protection of neonatal calves against bovine coronavirus-induced diarrhea by administrator of egg yolk or colostrum antibody powder", Veterinary Microbiology, vol. 58, No. 2-4, pp. 105-111, Nov. 1997.
International Search Report and Written Opinion cited in PCT/US11/61708 dated Mar. 29, 2012.
Japanese Office Action dated Sep. 29, 2105 for corresponding patent application JP 2013-540999, with English Translation.
Jin et al., "Effect of anti-RV immunoglobulin therapy on infants with rotavirus enteritis," Pediatric Emergency Medicine, Dec. 2004, vol. 11, No. 6, pp. 366-368.
Karge et al., "Pilot Study on the Effect of Hyperimmune Egg Protein on Elevated Cholesterol Levels and Cardiovascular Risk Factors," Journal of Medicinal Food, 2(2):51-63 (1999).
Kuijper "*Clostridium difficile* Ribotype 027, Toxinotype III, the Netherlands," Emerging Infectious Diseases, 12(5):827-830 (May 2006).

(56) References Cited

OTHER PUBLICATIONS

Kuroki et al., "Passive protection against bovine rotavirus-induced diarrhea in murine model by specific immunoglobulins for chicken egg yolk"; Veterinary Microbiology; 37:135-146 (1993).
Kuroki et al., "Passive protection against bovine rotavirus in calves by specific immunoglobulins from chicken egg yolk", Arch Virol, 138:143-148 (1994).
Kuroki et al., "Field evaluations of chicken egg yolk immunoglobulin specific for bovine rotavirus in neonatal calves," Archives of Virology, vol. 142, No. 4, Apr. 1, 1997.
Lamberti et al., "Oral zinc supplementation for the treatment of acute diarrhea in children: a systematic review and meta-analysis", Nutrients, 5(11):4715-4740 (Nov. 2013).
Larsson et al., "Oral immunotherapy with yolk antibodies to prevent infections in humans and animals", Upsala J. MedSci., 108:129-140 (2003).
Liou et al., "Production of Egg Yolk Immunoglobulin Against *Escherichia coli* From White Leghorn and Lohmann Chickens," Journal of Animal and Veterinary Advances 10(18):2349-2356, (2011).
Liu et al., "Global, regional, and national causes of child mortality: an updated systematic analysis for 2010 with time trends since 2000", Lancet, 379(9832):2151-2161 (Jun. 9, 2000).
Lloyd et al., "The role of IgA immunoglobulins in the passive transfer of protection to Taenia taeniaeformis in the mouse," Immunology 34:939-945 (1978).
Losonsky et al., "Oral Administration of Human Serum Immunoglobulin in Immunodeficient Patients with Viral Gastroenteritis, A Pharmacokinetic and Functional Analysis" Journal of Clinical Investigation, 76:2362-2367 (Dec. 1985).
Louie, "Treatment of Cryptosporidiosis with Oral Bovine Transfer Factor1," Clinical Immunology and Immunopathology 44:329-334 (Apr. 15, 1987).
Maffei et al., Gastric pH and microflora of normal and diarrhoeic infants, Gut, 16, pp. 719-726 (1975).
Marcq et al., "Keep bacteria under control: Dietary modulation of gut microflora in farm animals by use of hen egg yolk antibodies," University of Liege 6 pages.
McLead et al., Orally Administered Bovine Colostral Anti-Cholera Toxin Antibodies: Results of Two Clinical Trials, Am. J. Med., 85(6):811-816 (Dec. 1988).
Mine et al., "Chicken egg yolk antibodies as therapeutics in enteric infectious disease: a review", Journal of Medicinal Food, 5(3):159-169 (Fall 2002).
Morrison, et al., "Chimeric human antibody molecules: Mouse antigen-binding domains with human constant region domains," Immunology, Proceedings of the National. Academy of Sciences USA, 81:6851-6855, (Nov. 1984).
Newburg et al., "Role of human-milk lactadherin in protection against symptomatic rotavirus infection", Lancet, 351(9110):1160-1164 (Apr. 18, 1998).
New Zealand First Examination Report dated Nov. 4, 2013 for corresponding New Zealand Patent Application.
New Zealand Further Examination Report dated Mar. 23, 2015.
Numan et al., Clostridium difficile-associated diarrhoea: Bovine anti-Clostridium difficile whey protein to help aid the prevention of relapses, Gut 2007;56:6, 888-889 doi:10.1136/gut.2006.119016., www.gutjnl.com.
O'Farrelly, et al., "Oral Ingestion of Egg Yolk Immunoglobulin from Hens Immunized with an Enterotoxigenic *Escherichia coli* Strain Prevents Diarrhea in Rabbits Challenged with the Same Strain," Infection and Immunity, 60(7):2593-2597 (Jul. 1992).
O'Horo, et al., "The role of immunoglobulin for the treatment of Clostridium difficile infection: a systematic review," International Society of Infectious Diseases, 13:663-667 (2009).
Otto et al., Randomized control trials using a table formulation of hyperimmune bovine colostrum to prevent diarrhea caused by enterotoxigenic *Escherichia coli* in volunteers, Scandinavian J. of Gastroenterology, 14:862-868 (2011).

Patel et al., "Pedimune in Recurrent Respiratory Infection and Diarrhoea—The Indian Experience—The PRIDE study," Indian Journal of Pediatrics, 73:585-592 (Jul. 2006).
Parreño, et al., "Milk supplemented with immune colostrum: Protection against rotavirus diarrhea and modulatory effect on the systemic and mucosal antibody responses in calves experimentally challenged with bovine rotavirus," Veterinary Immunology and Immunopathology, 136:12-27 (2010).
Playford et al., "Colostrum and milk-derived peptide growth factors for the treatment of gastrointestinal disorders"; American J of Clinical Nutrition; 72(1):5-14 (2000).
Playford, "Peptide Therapy and the Gastroenterologist: Colostrum and Milk Derived Growth Factors"; Clinical Nutrition, 20(16)(Supp 1):101-106 (2001).
Polson et al., "Improvements in the Isolation of IgY from the Yolks of Eggs Laid by Immunized Hens," Immunological Investigation 14(4):323-327 (1985).
Quezada-Tristan et al., "Biochemical parameters in the blood of Holstein calves given immunoglobulin Y-Supplemented colostrums," BMC Veterinary Research, vol. 10, No. 1, Jul. 14, 2014.
Quigley, "Passive immunity in newborn calves," Advances in Dairy Technology, vol. 14, Jan. 1, 2002.
Rahman et al., "Randomized placebo-controlled clinical trial of immunoglobulin Y as adjunct to standard supportive therapy for rotavirus-associated diarrhea among pediatric patients", Vaccine, 30(31):4661-4669 (Jun. 29, 2012).
Richard et al., "Diarrhea in early childhood: short-term association with weight and long-term association with length." Am J Epidemiol, 178(7): 1129-1138 (Oct. 2013).
Rump et al. "Treatment of diarrhoea in human immunodeficiency virus-infected patients with immunoglobulins from bovine colostrum", Clinical Investigator, 70(7):588-594 (Jul. 1992).
Sarker et al., "Successful treatment of rotavirus diarrhea in children with immunoglobulin from immunized bovine colostrum", The Pediatric Infectious Disease Journal, 17(12):1149-1154 (Dec. 1998).
Sarker et al., "Randomized, placebo-controlled clinical trial of hyperimmunized chicken egg yolk immunoglobulin in children with rotavirus diarrhea." J Pediatr Gastroenterol Nutr, vol. 32, No. 1, 2001, pp. 19-25.
Saturno et al., "Oral Immunoglobulin Therapy in a Child with Severe Clostridium Difficile Diarrhea," American Academy of Allergy, Asthma and Immunology, AAAAI 62$^{nd}$ Annual Meeting Mar. 3-Mar. 7, 2006, The Journal of Allergy and Clinical Immunology 117(2) S284:1A Abstract #1096 (Feb. 2006).
Schenkels et al., Biochemical Composition of Human Saliva in Relation to Other Mucosal Fluids, Crit. Rev. Oral Biol. Med., 6(2):161-175 (1995).
Scott et al., "Management of Persistent Rotaviral Diarrhea in Children with Cystic Fibrosis with Enteral Administration of Intravenous Immunoglobulin," American Academy of Allergy, Asthma and Immunology, AAAAI 60$^{th}$ Annual Meeting, San Francisco, CA, Mar. 19-Mar. 23, 2004, The Journal of Allergy and Clinical Immunology 113(2) S209 3A Abstract #734 (Feb. 2004).
Search Report dated Jan. 10, 2017 in corresponding Taiwan Application No. 105114213 and English language translation thereof, 2 pages total.
Selinger et al., "Resistance to infection of the external eye: the role of tears," Survey of Ophthalmology, 1979, vol. 24, No. 1, pp. 33-38.
Stelwagen et al., "Immune components of bovine colostrum and milk" Journal of Animal Science, Oct. 2008, 87, pp. 3-9.
Supplemental European Search Report and European Search Opinion dated Jul. 2, 2015.
Suzuki et al., "Effect of dietary anti-Helicobacter pylori-urease immunoglobulin Y on Helicobacter pylori infection"; Alimentary Pharmacology and Therapeutics; 20(Supp 1):185-192 (2004).
Tawfeek "Efficacy of an infant formula containing anti-*Escherichia coli* colostral antibodies from hyperimmunized cows in preventing diarrhea in infants and children: a field trial," International Journal of Infectious Diseases, 7(2):120-128 (2003).

(56) References Cited

OTHER PUBLICATIONS

Tsou, "Current status and prospective of passive immune-vaccinated egg antibody for controlling human and animal diseases," Biotechnology Bulletin, 2009, vol. 4, pp. 143-149.

UNICEF/WHO, Joint statement, "Clinical management of acute diarrhea", New York and Geneva: United Nations Children's Fund and the World Health Organization; pp. 8 (May 2004).

UNICEF/WHO, Diarrhoea: Why children are still dying and what can be done, 68 pages (2009).

Ushijima et al., "Bacteriostatic Activity of Bovine Colostrum," The Journal of the Japanese Association for Infectious Diseases, 1991, vol. 65, No. 1, p. 54-60, with English translation.

Van Dissel et al., "Bovine antibody-enriched whey to aid in the prevention of a relapse of Clostridium difficile-associated diarrhoea: Preclinical and preliminary clinical data", J. of Med. Microbiology, 54, pp. 197-205 (2005).

Vega et al., "Egg yolk IgY: Protection against rotavirus induced diarrhea and modulatory effect on the systemic and mucosal antibody responses in newborn calves," Veterinary Immunology and Immunopathology, 142:156-169 (2011).

Vega et al., "IgY antibodies protect against human Rotavirus induced diarrhea in the neonatal gnotobiotic piglet disease model", PLoS One, 7(8):e42788 (Aug. 2012).

Weiner et al., "Passive immunity against human pathogens using bovine antibodies," Clin. Exp. Immunol. vol. 116; pp. 193-205. 1999.

Wergifosse et al., Comparison of the pathogenic treponemes of human and animal origin, Infection and Immunity, vol. 57, No. 5, pp. 1629-1631 (May 1989).

World Health Organization, Geneva, "Global networks for surveillance of rotavirus gastroenteritis, 2001-2008," Weekly epidemiological record, , 47:421-428 (83rd Year, Nov. 21, 2008).

World Health Organization, Global Health Estimates (GHE): Global Burden of Disease DALY's 2000 2011. Available at www.who.int/healthinfor/global_burden_disease/en. Accessed Apr. 15, 2014. (PDF found at www.who.int/healthinfo/statistics/GlobalDALYmethods_2000_2011.pdf).

Xie et al. "Therapeutic effect of probiotics and oral IgY as supplementary drugs in the treatment of pediatric rotavirus enteritis: a comparative study" Zhongguo dang dai er ke za zhi = Chinese Journal of Contemporary Pediatrics, 15(11):1000-1005 (Nov. 2013). (Chinese With English Abstract).

Yang, et al., Crystalline Monoclonal Antibodies for Subcutaneous Delivery, PNAS, 100(12):6934-6939 (Jun. 10, 2003).

Ylitalo et al., "Antibodies in the treatment of acute rotaviral gastroenteritis", Acta Paediatrica, 87(3):264-267 (Mar. 1998).

Yokoyama et al., "Passive Protective Effect of Chicken Egg Yolk Immunoglobulins against Experimental Enterotoxigenic *Escherichia coli* Infection in Neonatal Piglets," Infection and Immunity, 60(3):998-1007, (Mar. 1992).

Yolken et al., "Antibodies to rotaviruses in chickens' eggs: a potential source of antiviral immunoglobulins suitable for human consumption", Pediatrics, 81(2):291-295 (Feb. 1988).

Zeitlin et al. "Preventing infectious diseases with passive immunization" Microbes and Infection, vol. 2, pp. 701-708, 2000.

Kollberg et al., "Oral Administration of Specific Yolk Antibodies (IgY) May Prevent Pseudomonas aeruginosa Infections in Patients with Cystic Fibrosis: A Phase I Feasibility Study"; Pediatric Pulmonology; 35(6):433-440 (2003).

Extended European Search Report for Application No. 18183215.5 dated Dec. 6, 2018.

"APS 45-18F1 Instantized Whole Colostrum Powder", APS BioGroup, dated Apr. 10, 2010, 13 pages total.

Certificate of Analysis, APS 45-18F1 Instantized Whole Colostrum Powder, 2011, two pages total.

Declaration or Timothy A. Hall under 37 CFR 1.132 and attachments, dated Nov. 19, 2015, 19 pages total.

* cited by examiner

COMPOSITIONS AND METHODS FOR TREATMENT IN BROAD-SPECTRUM, UNDIFFERENTIATED OR MIXED CLINICAL APPLICATIONS

CROSS-REFERENCES TO RELATED APPLICATIONS

This application is a continuation of U.S. application Ser. No. 13/302,836, filed Nov. 22, 2011, now U.S. Pat. No. 9,701,735, issued Jul. 11, 2017, which claims the benefit of U.S. Provisional Application No. 61/416,667, filed Nov. 23, 2010, to Timothy W. Starzl, of Boulder, Colo., entitled "Compositions and Methods for Treatment in Broad-Spectrum, Undifferentiated or Mixed Clinical Applications", the entire contents of each of which is incorporated herein by reference.

FIELD OF THE DISCLOSURE

The disclosure provides compositions and methods for passive immunization. In embodiments, compositions comprising a synergistic combination of specific polyclonal antibodies with a carrier matrix are provided. The disclosure provides effective and economical compositions and methods for the treatment of pathogenic infections in broad-spectrum, undifferentiated, or mixed clinical applications. In one embodiment, compositions and methods for the treatment of diarrhea and enteric infections are provided.

BACKGROUND OF THE DISCLOSURE

Antibodies, immunoglobulins, and other biological immune factors (referred to here collectively as antibodies), both natural and their synthetic analogues, are known therapeutic agents in humans and animals. Antibodies operate by binding (via non-covalent forces) between the antigen combining site on the antibody and a portion of the antigen called the antigenic determinant or epitope. Antibodies are capable of high degrees of specificity. For example, the field of monoclonal antibodies has developed largely under the impetus of producing ever more specific and precise binding characteristics. However, this high specificity can lead to excessively limited binding attributes, where agents or antigens that are functionally identical do not react identically with the immunoreagent or immunotherapeutic. Cross-reactivity on the other hand, usually considered an error or failure to achieve binding specificity, is the reaction between an antigen and an antibody that was generated against a similar but different antigen. Controlled cross-reactivity may constructively be used to broaden the binding range of the antibody.

Colostrum has evolved naturally in mammals specifically to deliver its components to neonates to and through the gastrointestinal tract in a very concentrated low-volume form. Colostrum is known to contain antibodies such as IgA, IgG, and IgM. Other components of colostrum include lactoferrin, lysozyme, lactoperoxidase, complement, and proline-rich polypeptides (PRP). A number of cytokines (small messenger peptides that control the functioning of the immune system) are found in colostrum as well, including interleukins, tumor necrosis factor, chemokines, and others. Colostrum also contains a number of growth factors, such as insulin-like growth factors I, and II, transforming growth factors alpha, beta 1 and beta 2, fibroblast growth factors, epidermal growth factor, granulocyte-macrophage stimulating growth factor, platelet-derived growth factor, vascular endothelial growth factor, and colony-stimulating factor-I.

The antibodies and cofactors in colostrum can, through breast feeding provide a passive immunity to the recipient. Normally antibodies and cofactors are passed to the neonate from the mother and provide the first protection against pathogens. Growth factors also stimulate the development and repair of the gut.

One condition that could be addressed by using passive immunity is diarrhea. Diarrhea is caused mainly by the ingestion of pathogens. According to the World Health Organization (WHO), eighty-eight percent of cases diarrhea worldwide are attributable to unsafe water, inadequate sanitation or insufficient hygiene. These cases result in about 1.5 million deaths each year, most being the deaths of children. (Pruss-Urstun et al., Safer water, better health: costs, benefits and sustainability of interventions to protect and promote world health. World Health Organization, Geneva, 2008. ISBN 978 92 4 1596435).

Of particular global concern are the instances of infectious diarrhea in the developing world, which are a cause of tremendous ongoing morbidity and mortality, particularly in the pediatric population. For example, India has one of the highest infant mortality rates in the world according to a 2009 United Nations Human Development report. For example, Save the Children, a global non-profit, reports that one child dies every 15 seconds in India, and 90% of these deaths are due to preventable diseases, such as diarrhea. Rotavirus and measles vaccines, handwashing with soap, improved drinking water supply and community-wide sanitation are recommended by WHO for the prevention of diarrhea; however, these measures are not effective to treat the disease.

Standard treatment protocol in much of the world for pediatric diarrhea includes a concomitant administration of antibiotics and oral rehydrative therapy. For many reasons, antibiotics are a prescription drug. Antibiotics are not effective in the treatment of viral infection. For example, rotavirus is estimated to cause about 40 percent of all hospital admissions due to diarrhea among children under five years of age worldwide. (Weekly Epidemiological Record, vol. 83, no. 47, 21 Nov. 2008). The inappropriate use of antibiotics can promote resistant strains of bacteria. Conversely, the infection may be caused by a resistant strain of bacteria. Even under the best of circumstances, use of an appropriate antibiotic may take several days to reduce the severity of the symptoms of diarrhea.

Another disadvantage of antibiotics is that administration can induce the destruction of both pathogenic and benign bacteria found in the GI tract which can further result in release of endotoxic lipopolysaccharides. (Holzheimer, The significance of endotoxin release in experimental and clinical sepsis in surgical patients—evidence for antibiotic-induced endotoxin release? Infection. 1998 March-April; 26(2):77-84). These endotoxins have a host of adverse systemic effects including fever, changes in white blood cell counts, disseminated intravascular coagulation, hypotension, shock and death, malabsorption; in fact, the direct injection of fairly small doses of endotoxin results in death in most mammals. Todar K. *Bacterial Endotoxin*. Textbook of Bacteriology. 2008. textbookofbacteriology.net.

According to WHO, oral rehydration therapy and zinc with continued feeding, including breastfeeding, is recommended for treatment of childhood diarrhea. Zinc syrup or zinc-fortified oral rehydration solution (ORS, 40 mg/L) is typically employed at a dose of about 15 to 30 mg per day. Zinc is inexpensive, but has modest efficacy. Zinc syrup results in only about a 25 percent reduction in duration of acute diarrhea, and a 40 percent reduction in treatment failure or death. (Bhutta et al. Therapeutic effects of oral zinc in acute and persistent diarrhea in children in developing countries: pooled analysis of randomized controlled trials. *The American Journal of Clinical Nutrition.* 2000; 72(6): 1516-22). One study evaluated the efficacy and safety of a zinc-fortified (40 mg/L) ORS among 1,219 children with acute diarrhea. Clinical outcomes among the zinc-fortified ORS group were modestly improved, compared with those for the control group, who received standard ORS only. In that study, the total number of stools was lower among the zinc-ORS group compared with the total number for the control group. No substantial effect on duration of diarrhea or risk for prolonged diarrhea was noted. (Bahl R, Bhandari N, Saksena M, et al. Efficacy of zinc-fortified oral rehydration solution in 6- to 35-month-old children with acute diarrhea. J Pediatr 2002; 141:677-82).

It is known that antibiotics are ineffective to treat a viral infection, such as a rotavirus infection. Other interventions have limited effectiveness. Additionally, appropriate diagnostic tools to distinguish the cause of diarrhea are not always readily available or affordable.

Clearly a rapid, effective and economical alternative for the treatment of undifferentiated diarrhea is desirable. There remains a need for effective, economical compositions and methods for treatment of diarrhea and enteric infections in broad-spectrum, undifferentiated, or mixed clinical applications.

SUMMARY OF THE DISCLOSURE

The disclosure provides compositions and methods of passive immunization wherein a specific binding molecule, such as a specific immunoglobulin, is combined with a carrier matrix to provide a composition for oral or mucosal administration for management of microorganisms; including treatment or prophylaxis of a pathogenic infection or undesirable strain. In embodiments, the compositions are administered to a non-neonatal subject.

In one embodiment, the disclosure provides a composition for administration to a non-neonate human for the management of microorganisms, the composition comprising at least one specific binding molecule, or fragment thereof, derived from the adaptive immune system of an animal, wherein the specific binding molecule is selected from an immunoglobulin, antibody, peptide, variable lymphocyte receptor, transfer factor, or a mixture thereof; and a carrier matrix comprising two or more components of the innate immune system of a non-human mammal, wherein the matrix can be selected from, or derived from the components of, colostrum, milk, serum, plasma, saliva, lymph fluid, mucous, or lachrymal fluid; wherein the matrix and the specific binding molecule are derived from different species.

In a preferred embodiment, the carrier matrix comprises bovine colostrum. In another embodiment, the matrix comprises the components of the innate immune system that are selected from lysozyme, phospholipase, defensins, opsonins, components of the complement system, betalysin, protein-rich peptides (PRP), (PRPs), lactoferrin, transferrin, cytokines, interleukins, chemokines, interferons, TNF-alpha, fibronectin, leukocytes, white blood cells, phagocytes, macrophages, monocytes, neutrophils, polymorphonuclear cells, dendritic cells, mast cells, eosinophils, basophils, natural killer (NK) cells, lymphokine activated killer (LAK) cells, defensins, elastase, cathepsin G, myeloperoxidase, and NADPH oxidase.

In various embodiments, the composition includes a pharmaceutically acceptable carrier. In other embodiments, the composition includes a food grade carrier. In embodiments, the compositions can be administered via oral delivery, nasal delivery, ocular delivery or combinations thereof.

In other embodiments, the composition does not include an exogenously added polymer, copolymer, liposome, hydrogel or fibrin. In other embodiments, the composition does not include microspheres or microcapsules. In yet a further embodiment, the composition does not include an exogenously added antigen.

In a further embodiment, the specific binding molecules specifically bind to a pathogen, a pathogen related toxin, a pathogen related adhesion element, undesirable strain, or a combination thereof. In one aspect, the pathogen comprises a human or veterinary, enteric or gastrointestinal, pathogen causing gastroenteritis.

In various aspects, the pathogen or undesirable strain is selected from the group consisting of: *Campylobacter jejuni, Salmonella, Salmonella enterica* serovar *Typhi, Shigella dystenteriae, Plesiomonas shigelloides, Escherichia coli* [including (EPEC) enteropathogenic *E. coli*, (ETEC) enterotoxigenic *E. coli*, (EaggEC) enteroaggregative *E. coli*, (EIEC) enteroinvasive *E. coli*, and (EHEC) haemorrhagic *E. coli*], *Clostridium difficile, Yersinia enterocolitica, Vibrio cholerae* O1, *Vibrio* O139, Non-O1 *Vibrios, Vibrio parahaemolyticus, Aeromonas hydrophile, Clostridium perfringens, Clostridium difficile,* enterohepatic *Helicobacter* (including *Helicobacter pylori*), *Staphylococcus aureus, Klebsiella,* rotavirus, coronavirus, norovirus, calicivirus, enteric adenovirus, cytomegalovirus, astrovirus, *S. pneumoniae, H. influenzae, Neisseria gonorrhoeae,* herpes zoster virus, *Fusarium* spp., and *Acanthamoeba* spp.

In a specific aspect, the pathogen related toxin comprises an endotoxin or exotoxin.

In another specific aspect, the pathogen related adhesion element comprises adhesins, cadherins, cilia, fimbrillae, a viral adhesion structure, or a combination thereof.

In various embodiments, the composition is administered orally in an amount effective for the treatment or prevention of undifferentiated diarrhea, traveler's diarrhea, rotavirus diarrhea, toxin-mediated diarrhea, cholera, *C. difficile* infection, dysentery, typhoid fever, peptic ulcers, or for gastrointestinal flora management. In another aspect, an effective amount of the composition confers passive immunity to a subject.

In another embodiment, the disclosure provides a method for preparing the composition of the disclosure by the steps of: (a) obtaining from an animal at least one specific binding molecule or fragment thereof that binds to a specific antigen, wherein the specific binding molecule is selected from an immunoglobulin, antibody, peptide, variable lymphocyte receptor, transfer factor, and a mixture thereof; (b) obtaining at least one carrier matrix, comprising at least two components obtained from a nonhuman animal selected from the group consisting of enzymes, lactoferrin, transferrin, nonspecific immunoglobulins, cytokines, white blood cells, complement components, interferons, and fibronectin; (c) preparing a solid form of the carrier matrix and of the specific binding molecule or fragment thereof; and (d) mixing the solid form of the carrier matrix with the solid form of the specific binding molecule or fragment thereof.

In another embodiment, the present invention provides a method for preparing an immunity conferring composition. The method includes (a) obtaining at least one exogenously sourced specifically targeted immune factor; (b) preparing a powderized form of the at least one exogenously sourced specifically targeted immune factor; (c) obtaining at least one exogenously sourced carrier matrix, optionally mixed the exogenously sourced carrier matrix with a mixture of agents to support and interact with the exogenously sourced specifically targeted immune factor; (d) preparing a powderized form of the at least one exogenously sourced carrier matrix; and (e) mixing the powderized form of step (b) with the powderized form of step (d), thereby obtaining the passive immunity conferring composition. In one aspect, the passive immunity conferring composition includes a dose controlled formulation. In various aspects, the passive immunity conferring composition includes a pharmaceutically acceptable carrier. In various aspects, the passive immunity conferring composition does not include a polymer, copolymer, liposome, hydrogel, or fibrin. In various aspects, the passive immunity conferring composition does not include microspheres or microcapsules. In various aspects, the passive immunity conferring composition does not include an immunogen or antigen.

The present invention includes at least one of the following distinguishing attributes: (a) it enables customized design of the matrix, specific factors, and the activating events for specified or targeted diseases; (b) it enables dose controlled formulation of a variety of mixtures of components, which may be tuned or adjusted for effect; (c) it enables dose controlled formulation that provides specified components in excess of normal physiological levels that can be achieved in natural systems; (d) it uses complex multi-component multi-pathway interactions to create a systems effect that emulates a native immune system response; (e) it enables creation of a preconditioned or potentiated passive immune response that can be administered in its potentiated state, and subsequently activated by the presence of the target pathogens, toxins, disease state, or syndrome; (f) it enables the creation of formulations that have a defined specificity or broad-spectrum effect, to match the needs of the specific target disease state or syndrome, or of the practice environment within which the product is to be used; and (g) it enables the creation of formulations that can be targeted for prophylaxis as well as for therapeutic intervention.

In another aspect, by adjusting the amounts of the specific binding molecules, such as polyclonal antibodies, in the composition a dose controlled formulation can be prepared.

In a preferred embodiment, the at least one specific binding molecule comprises IgY derived from immunized chickens In other specific aspects, the IgY comprises a pool of IgY specific for at least enterotoxigenic *E. coli* spp., *E. coli* K99 pili adherence factor, *Clostridium perfringens toxoid, Salmonella typhimurium*, rotavirus, and coronavirus.

In another embodiment, the composition is topically administered to a mucosal membrane.

In another embodiment, the pathogen comprises a pathogen causing vaginitis. In various aspects, the pathogen is selected from the group consisting of: *Gardnerella* spp., *Neisseria gonorrhoeae, Chlamydiaceae trachomatis, Mycoplasma* spp., *Campylobacter jejuni, Trichomonas vaginalis*, herpes virus type 1, herpes virus type 2, *Candida albicans, Candida glabrata, Candida tropicalis, Candida parapsilosis* and *Candida krusei.*

In another embodiment, the pathogen is Group A *Streptococcus* bacteria.

In another embodiment, the pathogen comprises a pathogen causing conjunctivitis selected from the group consisting of *S. aureus, S. pneumoniae, H. influenzae, Neisseria gonorrhoeae, Chlamydia trachomatis*, adenovirus, herpes simplex, herpes zoster virus, enteroviruses, *Fusarium* spp, *Candida* spp. and *Acanthamoeba* spp.

In another embodiment, the compositions of the disclosure are useful as nutritional compositions for administering to a subject in need thereof who is afflicted with a disease that creates special dietary needs such as pediatric diarrhea, Crohn's disease, and ulcerative colitis.

BRIEF DESCRIPTION OF THE DRAWINGS

FIG. 1 shows average daily stool frequency over a five day period for two field trial test groups compared to negative control for the composition of Example 1A. In Trial 1 (n=29) and Trial 2 (n=31), the composition Example 1A is administered once daily for three days with antibiotic and oral rehydration salts (ORS). In the Negative Control (n=28), only antibiotic and ORS are administered without a composition of the disclosure.

FIG. 2 shows average daily stool consistency on a 1-5 scale (1=normal and 5=liquid) over the same five day period for the same three groups from FIG. 1.

FIG. 3 shows average physician assessed wellbeing on a 1-5 scale (1=normal and 5=severely ill) over the same five day period for the same three groups from FIG. 1.

FIG. 4 shows average daily stool frequency over a five day period for three field study (trial) test groups. Trials 1 and 2, and the negative control, are as described for FIG. 1. In Trial 3 (n=140), patients were administered the composition of Example 1B with antibiotic and ORS.

FIG. 5 shows average daily stool consistency on a 1-5 scale (1=normal and 5=liquid) over the same five day period for the same four groups from FIG. 4.

FIG. 6 shows average physician assessed wellbeing on a 1-5 scale (1=normal and 5=severely ill) over the same five day period for the same four groups from FIG. 1.

FIG. 7 shows average daily stool frequency over a five day period for Trials 1 and 2, negative control, Trial 3 is broken into 6 subgroups (ES204A): 2 g spray dried egg with 4 g colostrum administered for 3 days; (ES204B): 2 g spray dried egg with 4 g colostrum administered for 2 days; (MT204A) 2 g thermal dried egg with 4 g colostrum for 3 days; (MT304A) 3 g thermal dried egg with 4 g colostrum for 3 days; (MS204A) 2 g spray dried egg with 4 g colostrum for 3 days; (MS304A) 3 g spray dried egg with 4 g colostrum for 3 days.

FIG. 8 shows average daily stool consistency on a 1-5 scale (1=normal and 5=liquid) over the same five day period for the same groups from FIG. 7.

FIG. 9 shows average physician assessed well-being on a 1-5 scale (1=normal and 5=severely ill) over the same five day period for the same groups from FIG. 7.

DETAILED DESCRIPTION

Definitions

The terms "prevention", "prevent", "preventing", "prophylaxis" and as used herein refer to a course of action (such as administering a compound or pharmaceutical composition of the present disclosure) initiated prior to the onset of a clinical manifestation of a disease state or condition so as to prevent or reduce such clinical manifestation of the disease state or condition. Such preventing and suppressing need not be absolute to be useful.

The terms "treatment", "treat" and "treating" as used herein refers a course of action (such as administering a compound or pharmaceutical composition) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method, compound or pharmaceutical composition of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method, compound or pharmaceutical composition of the disclosure.

The term "individual", "subject" or "patient" as used herein refers to any animal, including birds or mammals, such as mice, Norway rats, cotton rats, gerbils, cavies, hamsters, other rodents, rabbits, dogs, cats, swine, cattle, sheep, goat, horses, or primates, and humans. The term may specify male or female or both, or exclude male or female. In one aspect, the patient is an adult human. In another aspect, the patient is a non-neonate human infant. In another aspect, the patient is a human toddler, child, or adolescent.

The term "neonate", or newborn, refers to an infant in the first 28 days after birth. The term "non-neonate" refers to an animal older than 28 days.

The term "effective amount" as used herein refers to an amount of an agent, either alone or as a part of a pharmaceutical composition, that is capable of having any detectable, positive effect on any symptom, aspect, or characteristics of a disease state or condition. Such effect need not be absolute to be beneficial.

The term "including" as used herein is non-limiting in scope, such that additional elements are contemplated as being possible in addition to those listed; this term may be read in any instance as "including, but not limited to."

The term "immunize", "actively immunize", "actively immunizing", and "active immunization" means to purposefully immunize a subject by exposing a subject to an antigen, for example, an antigen derived from a microorganism, such as but not limited to, a virus or a bacteria; such exposure may be carried out by exposing the subject to an intact organism, an attenuated organism, a portion of the organism, one or more antigens present on the organism or a combination of the foregoing.

The term "passively immunize", "passively immunizing", and "passive immunization" means to provide antibodies against an antigen, for example, an antigen derived from a microorganism, such as but not limited to, a virus or a bacteria, to a subject without necessarily eliciting an immune response to the organism in the subject. Passive immunization provides immediate protection but the subject does not develop memory cells as a result.

The term "passive immunity" as used herein refers to artificially acquired immunity achieved by the transfer of antibodies to the subject. The terms "egg" or "egg product" each mean an avian sourced whole shell egg (conventional, immunized or otherwise) or any product or fraction derived therefrom.

The terms "immune egg" or "immune egg product" each mean whole egg or any product or fraction derived therefrom, obtained from an egg producing animal maintained in a immunized state.

The term "antigen" refers to an entity or fragment thereof which can induce an immune response in an organism, particularly an animal. The term includes immunogens and regions thereof responsible for antigenicity or antigenic determinants.

The term "polyclonal antibody" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

The term "monoclonal antibody" is well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. "Monoclonal antibodies" are substantially homogenous populations of antibodies directed to a particular antigen or epitope. They may be obtained by any technique which provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

The term "crystalline" refers to an antibody, such as a monoclonal antibody that has been purified by crystallization, such as by batch crystallization. Crystalline antibodies can be used in order to generate a small volume, highly concentrated forms. (Yang et al., 2003, Crystallline antibodies for subcutaneous delivery. PNAS 100(12):6934-6939).

The term "undifferentiated diarrhea" means that the causative agent of the diarrhea is undiagnosed.

The term "antibody fragment" encompasses any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region. Antibody fragments include a portion of an antibody such as F(ab')2, F(ab)2, Fab', Fab, Fv, sFv and the like. Regardless of structure, an antibody fragment binds with the same antigen that is recognized by the intact antibody.

The term "transfer factor" refers to an immune molecule of approximately 5000 Daltons, made up of amino acids, that cause antigen-specific cell-mediated immunity, primarily delayed hypersensitivity and the production of lymphokines, as well as binding to the antigens themselves. (Kirkpatrick 1993, Structural nature and functions of transfer factors. Ann. N.Y. Acad. Sci. 685:362-368.)

The term "variable lymphocyte receptors" refers to lymphocyte-derived molecules discovered in jawless vertebrates such as the lamprey and hagfish. These animals possess a large array of variable lymphocyte receptors that are produced from only a small number of genes and that bind to pathogenic antigens in a similar way to antibodies, and with the same degree of specificity. (Alder et al., 2005, Diversity and function of adaptive immune receptors in a jawless vertebrate. Science, 310(5756):1970-1973).

The term "cell receptor" refers to the ligand binding moiety of the B-cell receptor; a membrane bound immunoglobulin molecule of one isotype (e.g., IgD, IgM, IgE). With the exception of the presence of an integral membrane domain, these are identical to their secreted forms.

The term "specific binding" in the context of the characteristics of specific binding molecules, also known as specific targeted immune factors, such as an antibody, antibody fragment, variable lymphocyte receptor, or transfer factor, refers to the ability to preferentially bind to a particular antigen that is present in a homogeneous mixture of different antigens. In certain embodiments, a specific binding interaction will discriminate between desirable and undesirable antigens (e.g., "target" and "non-target" antigens) in a sample, in some embodiments more than about 10 to 100-fold or more (e.g., more than about 1000- or 10,000-fold). In some embodiments, the specific binding molecule may specifically bind to an epitope shared among different species or strains of a microorganism as compared to non-shared epitopes. In certain embodiments, the affinity between an antibody and antigen when they are specifically bound in an antibody-antigen complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, or less than about $10^{-12}$ M or less.

The term "innate immune system", or non-specific immune system, refers to the cells, molecular components and mechanisms that defend the host from infection by other organisms in a non-specific manner. The cells and molecular components of the innate immune system recognize and respond to pathogens in a generic way, but unlike the adaptive immune system, it does not confer long-lasting or protective immunity to the subject. Innate immune systems provide immediate defense against infection. Vertebrates possess a second layer of protection, the adaptive immune system, which is activated by the innate response.

The term "adaptive immune system" refers to highly specialized, systemic cells and processes that recognize and respond to an antigen, for example, to eliminate, neutralize or prevent pathogenic growth. The system is highly adaptable due to somatic hypermutation (a process of accelerated somatic mutation) and V(D)J recombination (an irreversible genetic recombination of antigen receptor gene segments). Adaptive immunity is also referred to as acquired immunity and creates an immunological memory. An adaptive immune response is pathogen and antigen specific and there is a lag time between exposure and maximal response. An adaptive immune response is based on the principle of clonal recognition, such that upon first exposure to an antigen, primed lymphocytes either differentiate into immune effector cells or form an expanded pool of memory cells that respond to secondary exposure to the same antigen by mounting an amplified and more rapid response.

The term "animal" refers to the animal kingdom definition.

All pronouns are intended to be given their broadest meaning. Unless stated otherwise, female pronouns encompass the male, male pronouns encompass the female, singular pronouns encompass the plural, and plural pronouns encompass the singular.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

MODES OF THE DISCLOSURE

The disclosure provides compositions and methods useful in the management of undesirable strains or pathogenic microorganisms.

One embodiment of the present invention is based on a method to create a targeted antibody-based formulation embedded or subsumed within a carrier matrix, where the antibodies use a controlled form of cross-reactivity to multiple clusters of related target antigens, and where the carrier matrix contains support and cofactors that enhance the effect of the antibodies. The utility of such antibody/matrix formulations may include providing broad-spectrum therapeutic interventions under conditions where the class of causative agent, but not the precise or specific causative agent, is known or suspected or under circumstances where multiple (mixed) causative agents are active.

A novel approach to the use of antibodies in this manner has been developed, that takes advantage of both the specificity and cross-reactive attributes of antibodies, and then further utilizes the components within the carrier matrix to generate a multi-component in situ immune response. In this embodiment, antibodies are designed to bind to all of several closely related epitopes that represent a structurally related cluster of antigens. These antigens may differ markedly in other respects, and may originate from diverse sources, organisms, or species.

One embodiment of the invention involves the method of specific binding molecules (immune factors, for example antibodies), within the carrier matrix, where the specific binding molecules have specificity to a class of related antigens, and are specifically cross-reactive to different instances of members of that class. There exists a degree of structural similarity in related clusters of target antigens, without regard to the organism or pathogen that is the source of the antigen. Similarity in structure can result in a phenomenon known as "cross-reactivity" (the steric binding of a reactive molecule to an antigen other than the antigen intended). Cross-reactivity is often unintentional, and in most cases is considered a source of error and non-specificity. However, in this embodiment the extent and degree of cross-reactivity is controlled by various means to limit and channel its expression so as to provide desired characteristics.

This treatment confers passive immunity to patients. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative interventions.

The present invention is based on the seminal discovery that the use of an exogenously sourced (containing components obtained from an animal different from the animal to be treated) carrier matrix in conjunction with exogenously sourced (obtained or corresponding to immune factors obtained from an animal different form the animal to be treated) specifically targeted immune factors can be used to transport and introduce an effective multi-parameter immunity to a subject in need thereof.

In one aspect, the disclosure provides a composition comprising: a) a non-neonate human effective amount of at least one specific binding molecule, or fragment thereof obtained from an animal and that specifically binds to an antigen, wherein the specific binding molecule is selected from an immunoglobulin, antibody, peptide, variable lymphocyte receptor, transfer factor, and a mixture thereof and, b) a carrier matrix comprising at least two components obtained from a nonhuman animal selected from the group consisting of enzymes, lactoferrin, trnasferrin, nonspecific immunoglobulins, cytokines, white blood cells, complement components, interferons, and fibronectin, wherein the at least one specific binding molecule and the at least two components of the carrier matrix are obtained from different animals.

In another aspect, the disclosure provides a method for preparing the composition comprising: (a) obtaining at least one specific binding molecule or fragment thereof from an animal that binds to a specific antigen, wherein the specific binding molecule is selected from an immunoglobulin, antibody, peptide, variable lymphocyte receptor, transfer factor, and a mixture thereof; (b) obtaining at least one carrier matrix, comprising at least two components obtained from a nonhuman animal selected from the group consisting of enzymes, lactoferrin, trnasferrin, nonspecific immunoglobulins, cytokines, white blood cells, complement components, interferons, and fibronectin; (c) preparing a solid form of the carrier matrix and of the specific binding molecule or fragment thereof; and (d) mixing the solid form of the carrier matrix with the solid form of the specific binding molecule or fragment thereof.

In yet another aspect, the compositions of the disclosure are useful in the treatment or prevention of microbial infections. In embodiments, microbial infections include those caused by *Campylobacter jejuni*, *Salmonella*, *Salmonella enterica serovar Typhi*, *Shigella dystenteriae*, *Plesiomonas shigelloides*, *Escherichia coli*, enteropathogenic *E. coli*, enterotoxigenic *E. coli*, enteroaggregative *E. coli*, enteroinvasive *E. coli*, haemorrhagic *E. coli*, *Clostridium difficile*, *Yersinia enterocolitica*, *Vibrio cholerae* O1, *Vibrio* O139, Non-O1 *Vibrios*, *Vibrio parahaemolyticus*, *Aeromonas hydrophile*, *Clostridium perfringens*, enterohepatic *Helicobacter*, *Helicobacter pylori*, *Staphylococcus aureus*, *Klebsiella*, rotavirus, coronavirus, norovirus, calicivirus, enteric adenovirus, cytomegalovirus, and astrovirus. In embodiments, the compositions are useful to treat or prevent conditions such as undifferentiated diarrhea, traveler's diarrhea, rotavirus diarrhea, toxin-mediated diarrhea, cholera, *C. difficile* infection, dysentery, typhoid fever, peptic ulcers, vaginitis, or for gastrointestinal flora management.

In a specific embodiment, the compositions and methods of the disclosure are employed in the treatment or prevention of diarrhea. There are multiple diarrhea causing organisms including viruses, bacteria, parasites and protozoa. The primary causes of bacterial infection, for example in India, include *Escherichia coli* spp., Enterotoxigenic *E. coli*, Entero-adherent *E. coli*. *Auromonas* spp., *Camphylobacter jejuni*, *Shigella* spp., *Vibrio* spp., *Vibrio cholera* O1, *Vibrio parahaemolyticus*, *Salmonella* spp., *Staphylococcus aureus*, *Clostridium difficile*, *Clostridium perfringens*, and *Yersinia enterocolitica*. Secondary causes include *Clostridium difficile* (toxin A or B), The primary cause of viral diarrhea is infection by Rotavirus; although Calcivirus, Astrovirus, Norwalk virus, and Adenovirus are also known to cause diarrhea. Secondary causes of viral diarrhea include enteric adenovirus, herpes simplex virus and viral hepatitis. (John B. Sullivan and Gary R. Krieger, Clinical Environmental Health and Toxic Exposures, $2^{nd}$ Ed., Lippincott Williams & Wilkins, 2001, page 1040).

There are also known to be regional and seasonal differences in prevalence. For example, in Pranam, India, one study reported rotavirus accounted for an average 15-25% of childhood cases of diarrhea. Enterotoxigenic *E. coli* was responsible for 10 to 20% of total diarrhea cases, with Enteropathogenic *E. coli* causing about 1 to 5% of cases. *Camphylobacter jejuni* infection caused about 10 to 15%, and *Shigella* caused an estimated 5 to 15% of cases of childhood diarrhea. *Vibrio cholera* caused about 5 to 10% of cases. *Salmonella* (non-typhoid) caused about 1 to 5% of cases. Protozoan infection was caused by primarily by *Cryptosporidium* (5-15%). No pathogenic cause was identified in about 20 to 30% of cases. (Fricker, Children in the Tropics, Putting an end to diarrheal diseases, 1993-No. 204: 1-66).

Different regions within India ascribe bacterial cases of childhood diarrhea to different pathogens with different degree of prevalence. For example a study in Orissa, India found, among 866 culture-positive samples that *E. coli* sp. (75.5%), pathogenic *E. coli* (13.2%), *Aeromonas* spp. (2%), *Shigella* spp. (4.5%), *Vibrio cholera* O1 (17.3%), *V. cholera* O139 (1%) and *Salmonella* spp. (0.7%), find-health-articles.com/rec_pub_18806340-incidence.

Due to the wide variety of etiology, an effective, broad spectrum, economical and safe method of treating undifferentiated diarrhea is desired. A majority of childhood diarrhea cases seem to be caused by bacterial and viral infection, but an alternative to antibiotics and antiviral agents is desirable.

A. Compositions

One aspect of the disclosure involves composition useful in the treatment, prevention or management of microbial flora. In embodiments, the compositions are useful for treating pathogenic infections, in particular of the gastrointestinal tract.

In embodiments, the disclosure provides a composition comprising:

a) a non-neonate effective amount of at least one specific binding molecule, or fragment thereof obtained from an animal and that specifically binds to an antigen, wherein the specific binding molecule is selected from an immunoglobulin, antibody, peptide, variable lymphocyte receptor, transfer factor, and a mixture thereof; and, b) a carrier matrix comprising at least two components obtained from a nonhuman animal selected from the group consisting of enzymes, lactoferrin, trnasferrin, nonspecific immunoglobulins, cytokines, white blood cells, complement components, interferons, and fibronectin, wherein the at least one specific binding molecule and the at least two components of the carrier matrix are obtained from different animals.

Specific Binding Molecules

The compositions and methods of the disclosure provide specific binding molecules or fragments thereof obtained from an animal and that specifically bind to an antigen. A specific binding molecule includes an antibody, an antibody fragment, a peptide, a variable lymphocyte receptor, a transfer factor, and a mixture thereof.

Antibodies

Antibodies, immunoglobulins, and other biological immune factors (referred to collectively as antibodies), both natural and their synthetic analogues, are known therapeutic agents in humans and animals.

Antibodies operate by binding (via non-covalent forces) between the antigen-combining site on the antibody and a portion of the antigen called the antigenic determinant or epitope. Antibodies are capable of high degrees of specificity. For example, the field of monoclonal antibodies has developed largely under the impetus of producing ever more specific and precise binding characteristics. However, this high specificity can lead to excessively limited binding attributes, where agents or antigens that are functionally identical do not react identically with the immunoreagent or immunotherapeutic. Cross-reactivity on the other hand, usually considered an error or failure, is the reaction between an antigen and an antibody that was generated against a similar but different antigen. Controlled cross-reactivity may constructively be used to broaden the binding range of the antibody.

One embodiment of the present disclosure is based on a method to create a targeted antibody-based formulation embedded or subsumed within a carrier matrix, where the antibodies use a controlled form of cross-reactivity to multiple clusters of related target antigens, and where the carrier matrix contains support and cofactors that enhance the effect of the antibodies. The utility of such antibody/matrix formulations may include providing broad-spectrum therapeutic interventions under conditions where the class of causative agent, but not the precise or specific causative agent is known or suspected or under circumstances where multiple (mixed) causative agents are active. A novel approach to the use of antibodies in this manner has been developed, that takes advantage of both the specificity and cross-reactive attributes of antibodies, and then further utilizes the components within the carrier matrix to generate a multi-component in situ immune response. In this embodiment, antibodies are designed to bind to all of several closely related epitopes that represent a structurally related cluster of antigens. These antigens may differ markedly in other respects, and may originate from diverse sources, organisms, or species.

For the purposes of this disclosure, antibodies may be either monoclonal, polyclonal derived from any animal, fragments, chimeric, humanized or any other form, and antibodies may be of any isotype: for example IgA, IgD, IgE, IgG and IgM (placental mammals), IgY (chicken), or others, may be a bispecific or bifunctional, or multispecific or multifunctional antibody or fragment thereof. In embodiments, the specific binding molecule can be selected from one of three main categories: mammalian monoclonal antibodies, mammalian polyclonal antibodies, and avian polyclonal antibodies; or any fragments derived therefrom that retain the ability to bind to the pathogenic component.

One embodiment of this invention is its use in the production of a broad spectrum therapeutic. One method for producing this type of reactive formulation involves the production of polyclonal antibodies harvested from an appropriately immunized animal, and where such antibodies are then embedded in a carrier matrix. Polyclonal antibodies (or antisera) are antibodies that are derived from from different B cell lines. They are typically harvested en-mass from the serum, milk, colostrum, eggs, or biological fluids of an immunized animal. They are a mixture of immunoglobulin molecules secreted against a specific antigen, or group of antigens, recognizing a range of different epitopes. It is possible to have multiple antibodies for a single antigen (binding to different epitopes) or for a single antibody to bind to multiple antigens due to cross-reactivity. The polyclonal antibodies can be obtained from animals, such as cattle, sheep, horses, goats, swine, rabbits, chickens, ducks, geese, or turkeys that have been vaccinated or inoculated with antigens derived from target components. The antibodies can be harvested from, for example, tissue, serum, milk or eggs produced by, or derived, from the inoculated animal. This is in contrast to monoclonal antibodies, which are identical and monospecific; being produced by one type of immune cell that are all clones of a single parent cell.

The antibodies used in this invention may be collected from serum, plasma, colostrum, milk, eggs, or other suitable biologically derived fluid, or from cell culture media, supernatant, etc. The antibodies used in this invention may be treated in any suitable manner to prepare for formulation and use, including but not limited to separations, plasmapheresis, drying processes, lyophilization, pasteurization, and preservation methods. The antibodies used in this invention may be treated, concentrated, separated, or purified in various ways depending upon their final intended use.

By altering the mix of antibodies to those appropriate to various embodiments, the disclosure provides compositions and methods appropriate for treating or preventing other gastrointestinal infections such as cholera, *C. difficile*, dysentery, *Salmonella typhi* (typhoid fever), and *H. pylori* (peptic ulcers).

In one embodiment, antibodies are preferably raised in animals by, e.g., multiple subcutaneous (sc) or intraperitoneal (ip) injections of the relevant antigen and optionally an adjuvant. In one aspect, it may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or R N=C=NR, where R and R are different alkyl groups. Animals are immunized against the antigen, immunogenic conjugates, or derivatives as described herein. In other embodiments, the antibodies may be synthetic or semisynthetic, for example, as are obtained in a phage display library, or prepared as humanized or chimeric antibodies.

Birds (such as laying-hens) are highly cost-effective as producers of antibodies compared with mammals traditionally used for such production. Avian antibodies have biochemical advantages over mammalian antibodies. Immunologic differences between mammals and birds result in increased sensitivity and decreased background in immunological assays; as well as high specificity and lack of complementary immune effects when administered to mammalian subjects. In contrast to mammalian antibodies, avian antibodies do not activate the human complement system through the primary or classical pathway nor will they react with rheumatoid factors, human anti-mouse IgG antibodies, staphylococcal proteins A or G, or bacterial and human Fc receptors. Avian antibodies can however activate the non-inflammatory alternative pathway. Thus avian antibodies offer many advantages over mammalian antibodies.

In a preferred embodiment, the specific molecules are polyclonal antibodies prepared in eggs of hens inoculated with one of or a mixture of pathogenic components. Various preparations of specific antigens can also be employed for inoculation. After inoculation, the hen produces eggs containing substantial quantities of specific IgY immunoglobulin in the yolk, as well as small amounts of IgM and IgA immunoglobulins in the albumin. Therefore eggs are an excellent source for large quantities of economically produced, highly specific and stable antibodies. In one embodiment, chickens are used to produce avian antibody; however, turkeys, ducks, geese, ostriches, etc. may alternatively be used. In one aspect, hens are inoculated by any method known in the art, as described herein. For example, the antigen may be injected intramuscularly or subcutaneously. The preferred muscle for injection in an avian is the breast muscle. Other methods of administration that can be used include subcutaneous injection, intravenous injection, intraperitoneal injection, intradermal, rectal suppository, aerosol or oral administration.

The specific immune state is preferably induced and maintained in the target animal by immunization and repeated booster administrations of an appropriate dosage at fixed time intervals. The time intervals are preferably 1-8 week intervals over a period of 1-12 months. Dosage is selected between about 0.01-5 milligrams of the antigen. In one aspect, the dosage is 0.01 mg to 1.0 mg of antigen per inoculation, preferably 100 mg, 200 mg, 250 mg, 300 mg, 400 mg, 500 mg or 750 mg antigen per inoculation of a hen chicken. The total number of vaccinations can be selected from 1, 2, 3, 4, 5, or 6 in a 12 month period. Typically, a first inoculation is performed on day 1, with booster vaccinations on day 10, and day 20. The hen chicken can be re-vaccinated as needed by monitoring the specific antibody concentration, or titer, in the eggs by, e.g., ELISA. A typical subcutaneous dosage volume for a hen chicken is selected from between about 0.2 to 1.0 mL, 0.3 to 0.7 mL, or 0.5 mL. However, it is essential that the booster administrations do not lead to immune tolerance. Such processes are well known in the art.

It is possible to use other inoculation maintenance procedures or combination of procedures, such as, for example, intramuscular injection for primary immunization and intravenous injection for booster injections. Further procedures include simultaneously administering microencapsulated and liquid immunogen, or intramuscular injection for primary immunization, and booster dosages by oral administration or parenteral administration by microencapsulation means. Several combinations of primary and booster immunization are known to those skilled in the art.

Adjuvants, also known as pharmaceutical carriers, or functional equivalents hereof may be included in the immunization solution/vaccine composition to enhance the specific immune response of the animal. A large number of adjuvants have been described and used for the generation of antibodies in laboratory animals, such as mouse, rats, rabbits and chickens. In such setting the tolerance of side effects is rather high as the main aim is to obtain a strong antibody response.

Adjuvants pertaining to the present disclosure may be grouped according to their origin, be it mineral, bacterial, plant, synthetic, or host product. The first group under this classification is the mineral adjuvants, such as aluminum compounds. Antigens precipitated with aluminum salts or antigens mixed with or adsorbed to performed aluminum compounds have been used extensively to augment immune responses in animals and humans. In one embodiment, the adjuvant in the immunization composition is from a bacterial origin. Adjuvants with bacterial origins can be purified and synthesized (e.g. muramyl dipeptides, lipid A) and host mediators have been cloned (Interleukin 1 and 2). Known chemical purification of several adjuvants of active components of bacterial origin includes: *Bordetella pertussis, Mycobacterium tuberculosis*, lipopoly-saccharide, Freund's Complete Adjuvant (FCA) and Freund's Incomplete Adjuvant (Difco Laboratories, Detroit, Mich.) and Merck Adjuvant 65 (Merck and Company, Inc., Rahway, N.J.). In a specific aspect, Freund's Complete Adjuvant or Freund's Incomplete Adjuvant is employed in the immunization compositions of the disclosure. Additionally suitable adjuvants in accordance with the present invention are e.g., Titermax Classical adjuvant (SIGMA-ALDRICH), ISCOMS, Quil A, ALUN, see U.S. Pat. Nos. 5,876,735 and 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735). *B. pertussis* is of interest as an adjuvant in the context of the present invention due to its ability to modulate cell-mediated immunity through action on T-lymphocyte populations. Freund's Complete Adjuvant is the standard in most experimental studies. Mineral oil may be added to the vaccination composition in order to protect the antigen from rapid catabolism.

Many other types of materials can be used as adjuvants in immunogenic or immunization compositions according to the present disclosure. They include plant products such as saponin, animal products such as chitin and numerous synthetic chemicals.

Chickens immunized by the intramuscular route can produce high specific antibody levels in their eggs by day 28 after immunization and continue producing specific antibodies during more than 200 days making antibody preparations available in a short period of time, e.g. less than 4-5 weeks. Eggs contain IgY antibody concentrations of from up to about 50 to about 100 mg per egg. Over 100 mg of purified IgY can be obtained from a single egg. The percentage of antigen specific antibodies in one egg yolk can be up to about 2% to 10%. (daSilva et al., IgY: A promising antibody for use in immunodiagnostic and in immunotherapy. Veterinary Immunol. Immunopath, 135(2010):173-180). One chicken of a high egg-laying strain can produce around 20 eggs per month. Eggs weigh from about 33 to about 77 grams, with about 10.5% of the whole egg due to shell. The yolk is about 31% of the weight of the whole egg. Upon drying, about 1 kg of dried whole egg powder can be produced from 72 eggs. Therefore, in this calculation, one egg can return about 13.9 g dried whole egg. In another aspect, one immune egg can return from 10 g to about 15 g dried whole egg. In another aspect, the immune eggs of the disclosure are from 40 to 55 mL per egg with about 1-2 mg/mL total IgY per egg. In another aspect, immune eggs of the disclosure contain about 0.01 mg/mL to 0.05 mg/mL specific IgY per egg. Therefore, in one aspect after processing, one dried whole immune egg contains about 80 to 110 mg total IgY and about 6 to 10 mg of total mixed antigen-specific IgY, e.g., from a chicken immunized with, for example a mixed antigen preparation.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of immunogen necessary to induce an immune response depends on the vaccination procedure used, including the type of adjuvants and formulation of immunogen(s) used as well as the type of egg-producing animal used as the host.

In one embodiment, hen chickens suitable for the commercial production of eggs are employed in the production of polyclonal antibodies. Any breed of chicken appropriate for egg production can be employed. For example, Rhode Island Reds, White Leghorns, Brown Leghorns, Lohmann Brown hens, sex-linked hybrid crosses, or other breeds suited to large egg size, high volume egg production and ease of handling can be selected. In one aspect, chickens are inoculated as chicks as for standard diseases (e.g. *Salmonella*, avian influenza, or Newcastle virus etc.). In one aspect, chickens of any age can be inoculated. Hens which are about to reach laying age, about 15-19 weeks for chickens, or any preselected time before or thereafter, are inoculated on a schedule predetermined by the amount and timing of final product to result in a steady continuous production stream. Typically, after a suitable period of isolation and acclimatization of about 2 to 4 weeks, each group will enter into an inoculation program using various antigens or immunization compositions comprising specific antigens to which an antibody is desired.

In one embodiment, the eggs are collected from inoculated chickens and processed as whole eggs. Eggs are stored under refrigeration conditions until enough are collected to prepare a batch. Batches of eggs from predetermined groups of chickens are cracked, the contents are separated from the shells and mixed and preferably pasteurized to eliminate potential contamination from pathogenic microorganisms from the chicken.

In one aspect, the immune egg products are pasteurized. Egg products are processed in sanitary facilities. Shell eggs are processed into immune egg product by automated equipment that removes the shell eggs from flats, washes and sanitizes the shells, breaks the eggs. Optionally, the whites are separated from the yolks. The liquid egg product is optionally filtered, optionally mixed with other ingredients, and is then chilled prior to additional processing. The resulting egg products liquid then receives a lethality treatment such as pasteurization or is heated in the dried form. In the U.S., the 1970 Egg Products Inspection Act (EPIA) requires that all egg products distributed for consumption be pasteurized.

Following pasteurization, the total egg content is dried using standard commercial methods, such as spray drying using ambient or hot air, thermal drying, freeze drying, or lyophilization. In one aspect, an appropriate method of drying the pasteurized liquid egg minimizes damage to the antibodies and molecular components in the egg, resulting in a product that has a high nutrient value and is capable of conferring passive protection.

In one aspect, the dried egg is tested to determine overall titer or antibody level. Standard test procedures are used, such as ELISA, FIA (fluorescent immunoassay), RIA (radioimmunoassay), or the like. In another aspect, the batch is blended with batches from groups of chickens at other average production levels resulting in a lot containing a standardized amount of antibodies. The dried egg containing specific polyclonal antibodies may be stored in an airtight container at room temperature prior to formulation into the compositions of the disclosure. In embodiments, the dried egg material is used as a whole egg and is not separated out. In embodiments, the whole dried egg material contains at least 5 mg per egg of specific IgY.

In another embodiment, IgY is isolated. The first step in the isolation of IgY is to separate the water-soluble proteins from lipoproteins. Water-soluble proteins constitute 42.4% of the total proteins in egg yolk (Osuga et al., "Egg Proteins: In Food Proteins, J. R. Whitaker and S. R. Tannenbaum eds., AVI Pub. Co., Westport, Conn. (1977)).

Many methods have been used for the isolation and purification of immunoglobulins from egg yolk (Martin et al., Can J. Biochem. Physiol. 35:241 (1957); Martin et al., Can. J. Biochem Physiol. 36:153 (1958); Jensenius et al., J. Immunol. Methods 46:63 (1981); Bade et al., J. Immunol. Methods 72:421 (1984); Polson et al., Immunol. Invest. 14:323 (1985); Hassl et al., J. Immunol. Methods 110:225 (1988)). Hatta et al. (Agric. Biol. Chem. 54:2531 (1990)) used food-grade natural gums (e.g., carrageenan) to remove yolk lipoprotein as a precipitate and to recover IgY in the water-soluble fraction from egg yolk. Methods for recovering antibodies from chicken egg yolk are well known in the art. Several methods can be used for the extraction of IgY from egg yolk, and commercial extraction kits are available (van Regenmortel, M. H. V. (1993). Eggs as protein and antibody factories. In Proceedings of the European Symposium on the Quality of Poultry Meat, pp. 257-263. Tours, France: INRA).

In another embodiment, the steric specific binding molecule may be a monoclonal antibody specific for a pathogenic component.

Monoclonal antibodies may be made using the hybridoma method first described by Kohler et al., Nature. 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem. 107:220 (1980).

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr.

Opinion in Immunol., 5:256-262 (1993) and Plíckthun. Immunol. Revs. 130:151-188 (1992).

In a further embodiment, monoclonal antibodies or antibody fragments can be isolated from antibody phage libraries generated using the techniques described in McCafferty et al. Nature. 348:552-554 (1990). Clackson et al. Nature. 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology. 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Antigens for Immunization to Prepare a Specific Binding Protein

The antigens selected for immunization can be bacterial, viral, protozoal, fungal, parasitic, cellular, or any other substances to which the immune system of an animal will respond. In one aspect, the immunogenicity of the antigens is enhanced by use of an adjuvant.

In one aspect, the animal is inoculated with the pathogenic components, antigens, or immunogens in a vaccination composition, inoculant or vaccine. In one aspect, the pathogenic components or specific antigens can be obtained or derived from commercial sources such as the American Type Culture Collection (ATCC). In another aspect, the pathogenic components can be isolated from a wild type strain. In another aspect, the pathogenic components or undesirable strains are present in a mixed antigen preparation. Any antigens or combination of antigens derived from various undesirable strains or pathogenic components can be employed in the immunization composition.

In one aspect, the inoculant, antigen or immunogen is selected to a common or preserved component or region of the targeted antigen cluster, while ignoring the variable or distinguishing components or regions of the individual members of the cluster of related antigens. The method involves the preparation of an appropriate immunogen with characteristics that elicit the production of antibodies that are cross-reactive to desired instances of that epitope, but which are not reactive to other epitopes, and the inoculation or exposure of the producing cells or organism to that immunogen so as to cause the production of antibodies, with the resultant antibodies being embedded within the suitable carrier matrix for administration. Formulations of this type may be developed that use admixtures of antibodies produced according to this method to provide broad coverage of more than one cluster of target antigens. For example, in the case where two clusters of unrelated antigens are associated with a disease or condition, and it is desirable to create a single formulation to address this disease or condition, an admixture of two antibodies, immunoglobulins, or biological immune factors may be prepared using this method that simultaneously provides two broad domains of reactivity. One example of this embodiment is for the production of antitoxin antibodies that are specifically reactive to clusters of structurally related toxins.

In one embodiment, this approach is used to make a broadly reactive antibody to lipopolysaccharide (LPS) (endotoxin) from any Gram-negative bacteria (*Escherichia coli, Salmonella, Shigella*, and other Enterobacteriaceae, *Pseudomonas, Moraxella, Helicobacter, Stenotrophomonas*, and others), or for example a broadly reactive antibody to AB5 toxins (including *Campylobacter* enterotoxin, cholera toxin, heat-labile enterotoxins (LT and LT-II) (*E. coli*), pertussis toxin, shiga toxin (*Shigella*), shiga-like toxin (or verotoxin)).

In a preferred aspect, these example anti-toxin antibodies have effect without regard to the species originating the toxin. In another aspect, the antibodies produced are neutralizing antibodies, capable of neutralizing or inactivating the biological activity of the target toxins. Such a broad-spectrum neutralizing antibody could be used to intervene in pathology cases (for example certain types of diarrhea) where the toxin mediating the symptoms was one of the cluster targeted (in these examples, AB5 or LPS), without requiring knowledge of which organism was causative. Further, if an admixture was prepared containing both the anti AB5 antibody and the anti LPS antibody in clinically effective amounts, the formulation could be used to intervene in case where the active toxin was either AB5 or LPS or both.

This method can be extended to include any number of (in this example) toxin clusters, and to include broad-spectrum neutralizing antibodies to mediators of other toxin-like reactions (for example viral toxin-like phenomena), to create a broadly applicable intervention (in this example to) diarrhea where symptoms and pathology can be managed without knowledge of the infectious causes, or where there are multiple infectious causes. In one aspect, the disclosure provides a composition comprising a synergistic combination of anti-toxin antibodies combined in a carrier matrix.

In some embodiments, the methods and compositions of the invention are used for a variety of pathogens or agents including, without limitation, cholera toxin (*Vibrio cholera*), *E. coli* (including enterotoxigenic (ETEC)), *Shigella, Salmonella, Campylobacter, Clostridium difficile*, parasites (e.g., *Giardia, Entamoeba histolytica, Cryptosporidiosis, Cyclospora*), and diarrheal viruses (e.g., rotavirus).

After entering the gastrointestinal tract many pathogens, including but not limited to bacteria such as *E. coli*, bind (adhere) to epithelial, mucosal, or other tissue and become embedded in gastrointestinal tract tissue, such as the wall of the intestine. After binding to tissue in the gastrointestinal tract the pathogens replicate, causing an increase in toxin concentrations, either directly from production or indirectly from increased lysing of pathogen cells by immune system action Inhibiting the ability of pathogens to bind to the gastrointestinal tract tissue promotes a more effective mobilization of the pathogens, digestion and excretion before colonies of sufficient size to cause lesions and other symptoms are formed. By blocking the class of receptors and ligands on the pathogen that would be used to adhere to the gastrointestinal tract, including but not limited to adhesins, cadherins, cilia, fimbrillae, and/or viral adhesion structures, adhesion to gastrointestinal tract tissue can be prevented or minimized, ultimately resulting in substantially decreased pathology from pathogens that utilize this mode of action.

In various embodiments, the pathogen is selected from one or a combination of human or veterinary, enteric or gastrointestinal, pathogens causing gastroenteritis. In various aspect, the pathogen is selected from the group consisting of: *Campylobacter jejuni, Salmonella, Salmonella typhimurium, Salmonella enterica* serovar *Typhi, Shigella dystenteriae, Plesiomonas shigelloides, Escherichia coli* [including (EPEC) enteropathogenic *E. coli*, (ETEC) enterotoxigenic *E. coli*, (EaggEC) enteroaggregative *E. coli*, (EIEC) enteroinvasive *E. coli*, and (EHEC) haemorrhagic *E. coli*], *Yersinia enterocolitica, Vibrio cholerae* O1, *Vibrio* O139, Non-O1 *Vibrios, Vibrio parahaemolyticus, Aeromonas hydrophile, Clostridium perfringens, Clostridium difficile,* enterohepatic *Helicobacter* (including *Helicobacter pylori*), *Staphylococcus aureus, Klebsiella,* rotavirus, coronavirus, norovirus, calicivirus, enteric adenovirus, cytomegalovirus, and astrovirus. In another aspect, the pathogen related toxin includes an endotoxin or exotoxin. In another aspect, the pathogen related adhesion element includes adhesins, cadherins, cilia, fimbrillae, a viral adhesion structure, or a combination thereof.

In various specific aspects the pathogenic components, immunogens or antigens can be derived from, e.g., Rotavirus, Corona virus; *Clostridium Perfringens* Type C; *Escherichia coli* (cellular); Enterotoxigenic strains of, and Enterotoxins from, *E. coli*; any bacteria having K99, K88, 987P, or F41 pili adherence factor antigen; endotoxin (or LPS) caused by *E. coli* and *Salmonella typhimurium* (gram negative bacteria, generally). In a particular aspect, hens are inoculated with antigens or toxins derived from one, two, three, four, five, six, seven, or eight, or a number of pathogenic microorganisms.

In one aspect, the immune response is more potent when the distance between the antigen source and the immune system of the vaccinated animal increases.

In a specific embodiment, a first flock of chickens is inoculated with a first one mixed antigenic preparation. In one aspect, a second flock of chickens is inoculated with a second mixed antigenic preparation containing a different set of antigens than the first. In another aspect, a third flock of chickens is inoculated with a third mixed antigenic preparation. In a further aspect, a fourth flock of chickens is inoculated with a fourth mixed antigenic preparation. While not meant to limit the scope of the invention, it is believed to be advantageous to immunize different flocks with different antigens in order to avoid antigen overload.

Eggs from each flock are collected, optionally titered as to specific and/or total IgY, optionally isolated and/or purified, and processed separately to prepare a dry powder. In another aspect, dry powdered eggs from the first and second; first, second and third; or first, second, third and fourth flocks are blended, or packaged, with a carrier matrix to prepare a composition of the disclosure. In one aspect, a first antigenic preparation comprises bovine rotavirus (serotypes G6 and G10), bovine coronavirus, enterotoxigenic strains of *Escherichia coli* having the K99 pili adherence factor, and *Clostridium perfringens* type C. The mixed antigenic preparation can be optionally adjuvanted to enhance the immune response.

In another aspect, a second antigenic preparation comprises beta toxin produced by *Clostridium perfringens* type C and enterotoxigenic strains of *Escherichia coli* producing heat-labile toxin or having the K99, K88, 987P, or F41 adherence factors.

In one aspect, a third antigenic preparation comprises *E. coli* and *Salmonella typhimurium*. JVAC reduces the incidence and severity of endotoxemia caused by *E. coli* and *Salmonella typhimurium*. Commonly associated with their endotoxins are Coliform Mastitis and other gram-negative diseases associated with Endotoxemia.

In another aspect, the antigens are prepared by any means known in the art. For example, cells from a wild type source, such as an animal suffering from, e.g., *E. coli* diarrhea. The isolate cells can be cultured in, e.g., Trypticase Soy Broth (TSB) at 37° C. overnight and concentrated by centrifugation. The resulting pellet can be re-suspended with 0.4% formaldehyde in PBS buffer and incubated at 37° C. for inactivation. Formaldehyde can be removed by centrifugation. The pellet can be resuspended in PBS and used as antigen. In one aspect, the antigens are emulsified with an equal volume of adjuvant prior to inoculation.

In another embodiment, the antigens are selected from those pathogenic organisms causing conjunctivitis. Known causative pathogens are described in US 2008/0031903, Gambotto et al., which is incorporated herein by reference.

Epidemic Keratoconjuctivitis (EKC) is a debilitating infectious disease of the eye that is seen all over the world. The disease is caused mostly by adenoviruses especially serotype 8, 19 and 37. Serotype 3, 4 and 11 were also implicated in some EKC epidemics. The disease affects all age groups, is highly contagious and spreads quickly in schools, schools, swimming pools, pediatric unit and camps. Treatment is presently symptomatic as there is no effective treatment. Development of effective anti-viral topical agent is desirable to treat the disease and prevent epidemic.

Conjunctivitis also can be caused by a number of additional bacterial, viral, fungal and protozoa agents, including, but not limited to: *S. aureus, S. pneumoniae, H. influenzae, Neisseria gonorrhoeae, Chlamydia trachomatis*, Adenovirus, Herpes Simplex, Herpes zoster virus, Enteroviruses, *Fusarium* species, *Candida* species and *Acanthamoeba* species. Certain viral infections, such as adenoviral infections may be treated with antiviral drug products, such as cidofovir. Typically, drug products have side effects, such as the ocular and renal side effects associated with cidofovir. Other logistical issues arise with drug products, including stability, cost of production, etc. As such, an inexpensive, readily-available, well-accepted and stable drug product for treatment of ocular infections is desirable.

In one aspect, the disclosure provides a composition for the treatment of conjunctivitis, or pink eye, comprising polyclonal antibodies to these pathogens combined in a carrier matrix as described below. The antibodies are produced as described herein.

In another embodiment, the antigens are selected from those pathogenic organisms causing vaginitis. The infection may be bacterial, fungal (yeast), or parasitic. Bacterial vaginitis can be caused, for example, by *Gardnerella* spp., *Neisseria gonorrhoeae, Chlamydiaceae trachomatis, Mycoplasma* spp., *Campylobacter jejuni*. Parasitic vaginitis can be caused by, e.g., *Trichomonas vaginalis*. Viral vaginitis can be caused by e.g., herpes virus type 1 or type 2. Candidal vaginitis is caused by yeastlike fungi *Candida*. There are more than 170 species of yeastlike fungi is described. *C. albicans* is the most frequent causative agent of a candidal vaginitis in 85-90% of women. *C. glabrata* (5-10%), *C. tropicalis* (3-5%), *C. parapsilosis* (3-5%) and *C. krusei* (1-3%) are also clinically significant among other species of

*Candida*. Any of these pathogens may be selected as the antigenic source for polyclonal antibody production as described herein.

Candidal vulvovaginitis is frequently caused by a number of predisposing factors, such as long and uncontrolled using of antibiotics, corticosteroids, cytostatics, oral contraceptives, radiation therapy, serious infectious disease, endocrine disorder, immunodeficiency state, etc. Prescription of broad spectrum antibiotics suppresses not only pathogenic bacteria, but also mucous vaginas saprophytes: lactobacilli and bifidobacteria. As a result vaginal pH raises (towards to alkaline range), and disturbance of self-cleaning processes occurs. Besides, *Candida* is able to use some antibiotics as nutrient substrates. Thus favorable conditions for active overgrowth of *Candida* arises in female genital organs. In one aspect, the disclosure provides a composition for the treatment of vaginitis comprising polyclonal antibodies to one or more of the described pathogens combined in a carrier matrix as described below.

In a specific aspect, the composition of the disclosure comprising a mixture of specific polyclonal antibodies in a carrier matrix provides a broad spectrum method of treating bacterial, viral, fungal or parasitic vaginitis. In another aspect, the compositions of the disclosure can be used to treat undifferentiated vaginitis in a subject in need thereof.

Other Specific Binding Molecules

The compositions and methods of the disclosure include other specific binding molecules including transfer factors, variable lymphocyte receptors and cell receptors. A transfer factor is an immune molecule of approximately 5000 Daltons, made up of amino acids, that cause antigen-specific cell-mediated immunity, primarily delayed hypersensitivity and the production of lymphokines, as well as binding to the antigens themselves. (Kirkpatrick 1993, Structural nature and functions of transfer factors. Ann. N.Y. Acad. Sci. 685:362-368.) Variable lymphocyte receptors are lymphocyte-derived molecules discovered in jawless vertebrates such as the lamprey and hagfish. These animals possess a large array of variable lymphocyte receptors that are produced from only a small number of genes and that bind to pathogenic antigens in a similar way to antibodies, and with the same degree of specificity. (Alder et al., 2005, Diversity and function of adaptive immune receptors in a jawless vertebrate. Science, 310(5756):1970-1973).

Carrier Matrix

The disclosure provides compositions for the treatment or prophylaxis of pathogenic infection in a subject. The compositions comprise specific binding molecules, such as polyclonal antibodies, combined with a carrier matrix. While not meant to limit the scope of the invention, the carrier matrix serves a dual purpose. First, to protect the antibodies in their intended functional environment, for example, upon oral administration, and within the gastrointestinal tract of the non-neonate subject; and further to provide components, e.g., components of the innate immune system, to react synergistically with the antibodies in the management of an infection.

The term "carrier matrix", or protective/reactive matrix, refers to any substrate, compound, formulation, or supplemental admixture (whether natural or synthetic) containing elements, co-factors, or other components in appropriate ratios and concentrations so as to supply elements required to propagate, promote, support, or enhance an in situ immune-type response, cascade, or reaction. These elements may variously promote cleavage and maturation reactions, the formation of assemblies and complexes, depletion and adsorption functions, supply essential elements, biologics, or compounds, and provide protective functions for active elements or components. A carrier matrix may or may not contain endogenous antibodies (immune factors), which may or may not be specific to targeted antigens.

In one embodiment, the carrier matrix the matrix is selected from, or derived from, serum, plasma, colostrum, milk, saliva, lymph fluid, mucous, or lachrymal fluid derived from a non-human mammal.

An example of a naturally occurring carrier matrix is colostrum. Colostrum has evolved naturally in mammals specifically to deliver its components to neonates to and through the gastrointestinal tract in a very concentrated low-volume form. Colostrum, or "first milk", is produced by mammals immediately postpartum. The antibodies and cofactors are passed to the neonate from the mother and provide the first protection against pathogens. Growth factors also stimulate the development and repair of the gut.

Colostrum contains a host of immuno-complimentary factors. They include interferons, immunglobulins (including IgG and secretory IgA), polymorphonuclear leukocytes, macrophages, and lymphocytes. Colostrum also contains proline-rich polypeptide, or PRP, a T-cell activator. Colostrum is known to be high in immunoglobulin content compared to milk. Colostrum is known to contain antibodies such as IgA, IgG, and IgM in mammals. IgA is absorbed through the intestinal epithelium, travels through the blood, and is secreted onto other Type 1 mucosal surfaces. Bovine Colostrum is noted to be anywhere from 6% to 20% immunoglobulin; primarily $IgG_1$ and $IgG_2$. In one aspect, whole bovine colostrum is used as the carrier matrix.

Colostrum also helps to regulate the intestinal environment, rendering it hostile to foreign pathogens. Colostrum contains lactoferrin, an iron-binding protein that prevents bacteria and viruses from obtaining iron necessary for replication. Colostrum also selectively fertilizes certain probiotic species that in turn help to ward off infection. It is the only natural source of two major growth factors, Transforming Growth Factors (TGF) alpha and beta, as well as a source of Insulin-Growth Factors 1 and 2. These factors promote tissue repair and development. Colostrum is also a source of Hepatocyte Growth Factor, which stimulates the growth and expansion of intestinal wall cells. Colostrum is naturally designed to serve as a carrier matrix within a gastrointestinal environment. Synthetic versions of a carrier matrix are also included in this disclosure. Carrier matrices that are composed of both natural and synthetic components are also included within the disclosure.

Colostrum is very rich in proteins, vitamin A, and sodium chloride, but contains lower amounts of carbohydrates, lipids, and potassium than normal milk. The most pertinent bioactive components in colostrum are growth factors and antimicrobial factors. The antibodies in colostrum provide passive immunity, while growth factors stimulate the development of the gut. They are passed to the neonate and provide the first protection against pathogens. The passive immunity from the mother gets transferred to the newborn.

Newborns have very small digestive systems, and colostrum delivers its nutrients in a very concentrated low-volume form. The gastrointestinal tract of the neonate is particularly receptive to passive transfer of immunity from colostrum. At birth gastric pH ranges vary from 6-8 due to residual amniotic fluid in the stomach. Gastric pH then falls to a pH of 1.5 to 3 in 24 to 48 hours. Therefore, The GI conditions of the newborn are conducive to passive immunization. In addition, gastric emptying time in neonates and premature infants is prolonged, with adult values being reached at 6-8 months of age. The antibodies and cofactors in colostrum can, under certain circumstances (e.g., breastfeeding) provide a passive immunity to the recipient; this is particularly true for the neonate. The gastrointestinal tract of non-neonatal babies, children, adolescents and healthy adults is a more hostile environment with respect to oral administration of immunoglobulins.

Other immune components of colostrum include the major components of the innate immune system, such as lactoferrin, transferrin, lysozyme, lactoperoxidase, complement, and proline-rich polypeptides (PRP). A number of cytokines (small messenger peptides that control the functioning of the immune system) are found in colostrum as well, including interleukins, tumor necrosis factor, chemokines, and others. Colostrum also contains a number of growth factors, such as insulin-like growth factors I, and II, transforming growth factors alpha, beta 1 and beta 2, fibroblast growth factors, epidermal growth factor, granulocyte-macrophage-stimulating growth factor, platelet-derived growth factor, vascular endothelial growth factor, and colony-stimulating factor-1.

In one aspect, the carrier matrix is comprised of two or more, three or more, four or more, five or more, or six or more, or seven or more non-immunoglobulin components of colostrum. In another aspect, the carrier matrix comprises colostrum that has been processed to remove the majority of immunoglobulins. In embodiments, a carrier matrix comprises at least two components obtained from a nonhuman animal selected from the group consisting of enzymes, lactoferrin, transferrin, nonspecific immunoglobulins, components of the complement system, cytokines, white blood cells, complement components, interferons, and fibronectin, wherein the at least one specific binding molecule and the at least two components of the carrier matrix are obtained from different animals. In another aspect, the matrix is comprised of two or more agents selected from lysozyme, phospholipase, defensins, opsonins, proline-rich polypeptides (PRP), beta-lysin, lactoferrin, transferrin, cytokines, interleukins, chemokines, interferons, TNF-alpha, fibronectin, proline-rich polypeptides, insulin growth factor type 1, insulin Growth Factor type 2, derived platelet growth factor, epidermal growth factor, fibroblast platelet growth factor, transforming growth factor alpha, transforming growth factor beta, nerve growth factor, leptin, leukocytes, white blood cells, phagocytes, macrophages, monocytes, neutrophils, polymorphonuclear cells, and dendritic cells, mast cells, eosinophils, basophils, natural killer (NK) cells, lymphokine activated killer (LAK) cells, cationic proteins including defensins, proteolytic enzymes including elastase, cathepsin G, myeloperoxidase, NADPH oxidase components, or a combination thereof. In another aspect, the matrix includes a mixture of agents from the innate immune system. In a preferred aspect, the carrier matrix is comprised of non-hyperimmune bovine colostrum.

Bovine colostrum is produced by cows for their newborn calves. In many dairy cow herds the calves are not permitted to nurse; rather, they are fed colostrum and later milk from a bottle then a bucket. The colostrum is collected and processed for commercial uses. Various compositions including colostrum and processes for preparing colostrum have been disclosed in U.S. Pat. No. 5,846,569, U.S. 6,410, 058, U.S. 6,475,511, and U.S. 6,521,277, the contents of which are incorporated by reference in their entireties. Dried bovine colostrum is commercially available. In one specific aspect, the carrier matrix is commercial dried bovine colostrum.

Livestock husbands/breeders commonly bank colostrum from their animals. Colostrum produced on their own premises is considered to be superior to colostrum from other sources, because it is produced by animals already exposed to (and thus making antibodies to) pathogens occurring on the premises. Generally, colostrum from animals exposed to relevant pathogens will have superior immunological characteristics.

Bovine colostrum and its components are safe for human consumption, except in the context of intolerance or allergy to lactose or other components. Bovine colostrum from pasture-fed cows contains immunoglobulins specific to many human pathogens, including *Escherichia coli, Cryptosporidium parvum, Shigella flexneri, Salmonella, Staphylococcus*, and rotavirus, depending upon their natural exposure to these pathogens. Before the development of antibiotics, colostrum was the main source of immunoglobulins used to fight infections.

Hyperimmune colostrum represents an attempt to boost the effectiveness of natural bovine colostrum by immunizing cows with a specific pathogen. This approach is promising as antibodies are produced to the specific pathogens or antigens used in the original challenge. However, varying response to antigens, biological variability, and low production yield of colostrum have limited its clinical and commercial utility.

In one aspect, the disclosure provides a composition comprising colostrum that is not hyperimmune colostrum or that does not contain a measurable or significant amount of antibodies specific for the pathogenic or target antigen components. In another aspect, the disclosure provides a composition in which the carrier matrix contains various components of the innate immune system without a significant amount of either specific or non-specific antibodies.

In one embodiment, the colostrum can be processed to remove the majority of immunoglobulin, e.g., by absorbing the antibodies onto an affinity resin (e.g. Protein G or Protein A Sepharose; or Protein A or Protein G Agarose) in a batch or column format and retaining the eluate for further processing. Immunoglobulin can also be removed by gel filtration chromatography on Sephadex G-200 or DEAE Sephadex A-25 ion exchange chromatography. (Lloyd and Soulsby, Immunology, The role of IgA immunoglobulin in the passive transfer of protection to *Taenia taeniaeformis* in the mouse. 34, 939-945) These processes can be run on a column or a batch format by various methods and techniques known in the art.

In one specific embodiment, the carrier matrix includes colostrum. In one aspect, commercial colostrum is employed as the supportive/reactive matrix. In a preferred aspect, the commercial bovine colostrum is an agglomerated and instantized, pasteurized, full cream, whole colostrum powder produced from first milking colostrum only. In another aspect, the colostrum is processed at low pressures and low temperatures and is spray dried using indirect steam to maintain maximum bioactivity. In another aspect the commercial colostrum is from antibiotic free sources. In another aspect, the colostrum is subjected to microbiological analysis and is found to be negative, or below acceptable levels with respect to a variety of pathogens. In various other aspects, the colostrum is assayed for other contaminants such as nitrates, aflatoxin, nitrofuran, dioxins, melamine, and heavy metals and found to be negative or below specified levels.

In one embodiment, the invention may be composed of colostrums of several hyperimmunized sources, each targeting a different cluster or class of antigen, where the colostrums are admixed to provide a broad-spectrum antibody formulation.

In another embodiment, the carrier matrix is comprised of a reconstituted or artificial mucosal secretion such as tear fluid, nasal or bronchial mucous, cervical mucous, seminal plasma, sweat, blood plasma or saliva. Body fluids are known to contain several components in varying amounts. (Schenkels et al., Biochemical composition of human saliva in relation to other fluids, Crit. Rev. Oral Biol. Med., 1995, 6(2):161-175). Saliva contain mucins, acidic PRPs, alpha-amylase, basic PRPs, basic PRG, secretory IgA, cystatins, statherin, IgG, extra-parotid glycoprotein (EP-GP), VEGh (a lipocalin), histatins, lysozyme, kallikrein, lactoferrin, lactoperoxidase, haptocorrin, beta-microseminoprotein, IgM, albumin, and Zn-alpha2-glycoprotein. In one aspect, the carrier matrix comprises two or more, three or more, four or more, five or more, six or more, or seven or more of the components of body fluids.

Tear fluid, or lachrymal fluid, has many of the same components as saliva and has a particularly high concentration of secretory IgA, VEGh, lysozyme, and lactoferrin. In one aspect, artificial lacrimal fluids containing salts such as sodium chloride and the like as a main ingredient, or eye drops containing hydroxyethylcellulose, chondroitin sulfate or hyaluronic acid or xanthan gum (U.S. Pat. No. 7,875,271, which is incorporated herein by reference) as known in the art are fortified with two or more, three or more, four or more, five or more components of the body fluids as described and used as a carrier matrix for purified polyclonal antibodies, as described herein. In one aspect, a composition could be used to treat microbial infections of the eye, such as pink eye.

Cervical mucous contains mucins, alpha-amylase, lysozyme, lactoperoxidase, albumin, and beta-microseminoprotein. The matrix is formed by combination of two or more, three or more, four or more, five or more of these components as a carrier matrix in a composition with a steric specific binding molecule, such as anti-bacterial or anti-fungal polyclonal antibodies, prepared by the methods of the disclosure.

In one aspect, the disclosure provides a composition comprising a gum capable of fixing water or swellable in water, containing carboxymethylstarch combined with a cellulose as a permeating agent, which when put into contact with water form almost instantaneously gels and is readily applicable for vaginal application. Tablets comprising the antibody/matrix composition of the disclosure could for example comprise carboxymethylstarch and cellulose as described in U.S. Pat. No. 4,808,415, which is incorporated herein by reference. In a particular aspect, the antibacterial and antifungal polyclonal antibodies are combined in the matrix and formulated to provide a broad spectrum treatment for vaginosis. In one aspect, the composition is used to treat a vaginal bacterial infection, such as *trichomonas* infection, or fungal vaginosis, such as *candida* infection.

Saliva is a mucosal secretion present in the oral cavity and produced by salivary glands. Saliva serves protective functions such as tissue coating, lubrication, humidification, and remineralization of the teeth. Saliva also serves host defense functions with immunological activity, anti-bacterial, anti-viral and anti-fungal activity. Saliva also serves digestive activity with digestive enzymes, bolus formation and taste. Saliva contains various proteins such as histatins, and acidic proline-rich proteins that are unique to saliva. Saliva also contains proteins present in other body fluids such as lysozyme, mucins, statherins and immunoglobulins. Saliva contains proteins such as albumin and Zn-alpha-2-glycoprotein that originate in blood plasma. There is a known therapeutic value of bovine saliva. (Varshney et al., 1997, Therapeutic value of bovine saliva in wound healing: a histomorphological study, Indian J. Biol. May 1997, 35(5): 535-7). In one aspect, components of saliva could be useful, for example, in toothpaste or mouthwash, or other preparations for oral mucosal administration.

Bronchial mucous contains mucins, alpha-amylase, basic proline-rich polypeptides (PRPs), cystatins, statherin, EP-GP, lysozyme, beta-microseminoprotein, and albumin. In one aspect, the disclosure provides a composition comprising a steric specific binding molecule and a carrier matrix comprising two or more, three or more, four or more of the components of saliva or bronchial secretions. In one aspect, the composition with the carrier matrix is to be packaged in a dry format with the steric specific binding molecule, such as anti-Group A *Streptococcus* polyclonal antibodies prepared according to the disclosure. In one aspect, the dry formulation is reconstituted, for example in a saline solution, and administered as a throat spray for treatment of strep throat.

Other carrier matrices may be prepared to function in other use environments, for example for aerosolized (inhaled), ocular, topical, or other preparations.

In a specific embodiment, the specific binding molecule and the carrier matrix are derived from different species. In a further aspect, both the specific binding molecule and the carrier matrix are derived from non-human species. In another aspect, the specific binding molecule is derived from a non-mammalian animal. In another aspect, the carrier matrix is derived from a non-human mammal.

Formulations and Compositions

In one embodiment antibodies are harvested from the plasma, serum, or blood, colostrum, eggs, or other component of an inoculated animal or artificial production system (such as cell culture), then purified or treated, and added to a carrier matrix such as colostrum. The compositions allow are used as a delivery medium for, e.g., oral administration of the antibody formulation. This approach may provide an effective way of reliably scaling antibody production for formulation in this manner, so as to control titer, consistency, and continuous availability, for commercial use. In one embodiment antibodies are harvested from the eggs of an inoculated animal, and may be purified or treated or retained in the egg material, and added to bovine colostrums.

There is a clear need for low cost and effective treatments for many gastrointestinal pathogens, and orally administered antibodies are candidates for this role. In addition to having demonstrated efficacy, orally administered antibodies are typically non-immunogenic. They are considered typically well tolerated with no adverse side effects reported and comparatively no different reactions than a comparable ingested food product. Notably several products containing orally administered antibody have received GRAS (Generally Recognized as Safe) certification by the FDA.

One embodiment of this invention is a broad spectrum therapeutic or prophylactic antitoxin formulation composed of an admixture of broad-spectrum neutralizing antibodies, embedded within a carrier matrix, produced according to this method, for the purposes of allowing for effective administration across a wide range of unknown or undiagnosed conditions resulting in toxin mediated diarrhea.

One embodiment of this invention is a broad spectrum therapeutic or prophylactic anti-pathogen formulation, embedded within a carrier matrix, containing an admixture of broad-spectrum anti-pathogen antibodies produced according to this method.

One embodiment of this invention is a broad spectrum therapeutic or prophylactic anti-adhesin formulation embedded within a carrier matrix, containing an admixture of broad-spectrum anti-adhesin antibodies produced according to this method.

One embodiment of this invention is a broad spectrum therapeutic or prophylactic formulation embedded within a carrier matrix, containing an admixture of broad-spectrum antitoxin, anti-pathogen, and anti-adhesin antibodies produced according to this method.

One important limitation of using natural food based products is that preparations are limited to the results allowed by natural processes. The present invention allows for the selective addition of levels of specific antibodies and general immune factors (formulation) that are significantly higher than physiological levels that can normally be achieved in nature. The present invention also allows for a weighting of various factors in a manner so as to create greater specificity to targeted diseases, pathogens, or substances.

In one embodiment, the formulation comprising the specific binding molecule is a dry solid (egg powder) formulation. The powdered formulation is sealed in airtight packets, optionally layered with an inert gas. The formulation can be stored for extended periods of time at room temperature, under refrigeration, or frozen temperatures. In other embodiments, the dried composition is formulated into capsules or tablets for oral administration. In another embodiment, the formulation is compressed into chewable tablets.

Another embodiment of the present invention relates to the pharmaceutical acceptable diluents for formulating the composition, wherein said pharmaceutical acceptable diluents are selected from the group consisting of a lactose, mannitol, sorbitol, microcrystalline cellulose, sucrose, sodium citrate, dicalcium phosphate, or any other ingredient of the similar nature alone or in a suitable combination thereof; binder selected from the group consisting of gum tragacanth, gum acacia, methyl cellulose, gelatin, polyvinyl pyrrolidone, starch or any other ingredient of the similar nature alone or in a suitable combination thereof; excipients selected from the group consisting of agar-agar, calcium carbonate, sodium carbonate, silicates, alginic acid, corn starch, potato tapioca starch, primogel or any other ingredient of the similar nature alone or in a suitable combination thereof; lubricants selected from the group consisting of a magnesium stearate, calcium stearate or steorotes, talc, solid polyethylene glycols, sodium lauryl sulfate or any other ingredient of the similar nature alone; glidants selected from the group consisting of colloidal silicon dioxide or any other ingredient of the similar nature alone or in a suitable combination thereof; a sweetening agent selected from the group consisting of such as sucrose, saccharin or any other ingredient of the similar nature alone or in a suitable combination thereof; a flavoring agent selected from the group consisting of peppermint, methyl salicylate, orange flavor, vanilla flavor, or any other pharmaceutically acceptable flavor alone or in a suitable combination thereof; wetting agents selected from the group consisting of acetyl alcohol, glyceryl monostearate or any other pharmaceutically acceptable wetting agent alone or in a suitable combination thereof; absorbents selected from the group consisting of kaolin, bentonite clay or any other pharmaceutically acceptable absorbents alone or in a suitable combination thereof; retarding agents selected from the group consisting of wax, paraffin, or any other pharmaceutically acceptable retarding agent alone or in a suitable combination thereof.

In another aspect, the daily dose for the non-neonate human is standardized by any method of quantifying the specific antibodies. In one aspect, the dose of the composition is standardized by use of an ELISA to evaluate the concentration of specific anti-antigen antibody in the formulation. In one aspect, one dose of the oral composition effective to treat a pathogenic infection contains antigen-specific binding molecule in an amount from about 0.0001 mg to 20 mg; from 0.001 mg to 15 mg; from 0.01 to 10 mg; from 0.05 to 5 mg; from 0.1 to 1 mg of mixed antigen specific binding molecule.

The term "solid form" refers to a dried form of a specific binding molecule, or a dried form of a carrier matrix, or a solid dosage form comprising both the dried specific binding molecule and the carrier matrix as a powder, compressed tablet, troche, or capsule. In one aspect, the solid dosage form is intended for oral administration. In one aspect, the powder is a formulation for suspension. In one aspect, powdered dried immune egg and powdered dried colostrum are packaged in an airtight packet. Immediately prior to oral administration, the contents of the packet are suspended, or dissolved, in about a liquid and administered orally.

In one aspect, the composition may also be provided in a liquid form for administration.

In one aspect, one dose contains 1 g, 2 g, 3 g, 4 g, 5 g, 5 g, 6 g, or 7 g of dried immune egg and 1 g, 2 g, 3 g, 4 g, 5 g, 5 g, 6 g, or 7 g dried bovine colostrum. In one aspect, one dose of the dried dosage form contains 3 g dried immune egg product and 4 g dried bovine colostrum. In one aspect, one dose of the dried dosage form contains 2 g dried immune egg product and 4 g dried bovine colostrum. In one aspect, one dose of the dried dosage form contains 4 g dried immune egg product and 4 g dried bovine colostrum. In another aspect, the contents of a single dose packet are dissolved in about 2 ounces of water and administered orally.

Formulations for oral use may also be prepared as troches, chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

In various embodiments, the formulations of the disclosure provide a variety of advantages with respect to the prior art. In one aspect, the formulations of the disclosure comprising antigen-specific IgY and a carrier matrix of bovine colostrum have the advantage of being prepared in a rapid time period of within about 6 weeks, once the antigens of interest are identified. This allows easy reproducibility and standardization of the chicken vaccination protocol. In one specific aspect, different flocks of chickens are vaccinated with a single, mixed antigen preparation each, and then combined for a broad spectrum composition for the treatment of a pathogenic infection. In one specific aspect, three flocks of chickens are vaccinated with separate mixed antigen preparations then pooled to prepare a broad-spectrum composition for the treatment of undifferentiated diarrhea without knowledge of the causative microbial pathogens. This method has the advantage that the mix of antigen-specific antibodies in the composition can be tailored for a particular outbreak, region, or season, if desired. Finally, in embodiments, the specific binding molecule need not be separated from the whole dried egg for rapid preparation and long term storage.

In another aspect, the compositions of the disclosure are effective for oral administration in the treatment of a pathogenic infection in non-neonates. The gastrointestinal tract of the non-neonate is very acidic and less absorptive than the neonate, as described herein. In the examples of the disclosure, the compositions were effective for treating undifferentiated diarrhea in non-neonatal children of 6 months to 5 years of age. In another aspect, the compositions of the disclosure are effective to treat or prevent traveler's diarrhea in adults. The carrier matrix is a protective and reactive matrix for combination with the antigen-specific binding molecules. In another aspect, the compositions of the disclosure are provided in a powdered, solid form for suspension immediately prior to administration. In one aspect, the suspended, or reconstituted, dosage form has the advantage of being very palatable to infants and children, even when suffering from the symptoms of a pathogenic infection. This has the advantage that the full dose is easily administered and ingested by the subject suffering from the pathogenic infection.

In another aspect, the compositions of the invention can be used for administering broad-spectrum passive immunity in either treatment, or prophylaxis of pathogenic infection. In one aspect, a low level of immunization of chickens can be sufficient to prepare a composition with an effective amount of anti-antigen specific binding molecule to result in an effective, broad-spectrum formulation when administered with a carrier matrix.

Treatment or Prophylaxis of Pathogenic Infection

The compositions of the disclosure comprise a specific binding protein embedded within a carrier matrix. The compositions can be administered in any method suitable to their particular immunogenic or biologically or immunologically reactive characteristics, including oral, intravenous, buccal, nasal, mucosal, dermal or other method, within an appropriate carrier matrix. A specific embodiment involves the oral administration of the composition of the disclosure.

In various embodiments, the composition is administered as a prophylactic or therapeutic composition. In various aspects, the composition includes a pharmaceutically acceptable carrier. In various aspects, the composition does not include a polymer, copolymer, liposome, hydrogel, or fibrin. In various aspects, the composition does not include microspheres or microcapsules. In various aspects, the composition does not include an immunogen or antigen. The composition of the invention can be administered via oral delivery, nasal deliver, ophthalmic delivery, ocular delivery, mucosal delivery, or a combination thereof.

One embodiment of this invention uses oral administration. It has been demonstrated in both human and animal systems that oral (ingested) administration of antibodies, immunoglobulins, and other biological immune factors can have measurable effects on the course, severity and duration on diseases of, in, associated with, or influenced by, the gastrointestinal system.

The admixture of broad-spectrum antibodies is embedded in a within a carrier matrix, such as for example colostrums for oral administration. Colostrum serves to provide synergistic protective and efficacious attributes to the antibody formulation. Any combination of antibodies can be used in within a carrier, including but not limited to a combination of anti-pathogen, anti-toxin, and anti-adhesin antibodies.

In one aspect, the compositions of the disclosure are used to treat patients suffering from various pathogenic infections. The compositions and formulations for oral administration can be administered once, twice, three times, or four times a day for two, three, four, five, six, seven, eight, nine, 10, 11, or 12 consecutive days for the treatment of a pathogenic infection. In one aspect, the composition is administered twice per day for five days for the treatment of a pathogenic infection. In another specific aspect, the composition is administered once per day for three consecutive days for the effective treatment of undifferentiated diarrhea in non-neonatal children, or in the treatment of traveler's diarrhea in non-neonatal children or adults. In another aspect, the composition may be regularly administered for the prophylaxis of a pathogenic infection.

In the case of a composition for the treatment of a pathogenic infection of a mucosal membrane by topical administration to a mucosal membrane, the composition can be administered two to six times per day for a period of three to 12 days.

In a preferred embodiment, the disclosure provides a composition effective for treating undifferentiated diarrhea in non-neonate humans. The composition takes advantage of an effective polyclonal antibody production strategy (chicken innoculation, with antibody harvesting through eggs) to generate high specificity antibodies targeted to several of the causes of diarrhea pathology. In a specific embodiment, the composition comprises specific polyclonal antibodies in a carrier matrix that is commercial bovine colostrum.

In a preferred embodiment, the disclosure provides an economical composition for the effective treatment of undifferentiated pediatric diarrhea. The composition comprises a mixture of polyclonal antibodies, primarily IgY, specific for *E. coli, Salmonella* spp., rotavirus, gram negative bacteria, toxins produced by pathogens, and adhesins that enable pathogen attachment and colonization in the gastrointestinal tract.

In a specific aspect, the composition comprises an equivalent weight amount of dried immune egg product from each of three flocks inoculated with different antigens or different mixed antigen preparations is co-packaged with a specific weight amount of commercial dried non-hyperimmune bovine colostrum. In one aspect, 0.5 to 3 g. 0.7 to 2.0 g, 1.0 g, 1.3 g, or 1.5 g of dried immune egg product from each flock is added to a single dose packet. Preferably either 1.0 g or 1.3 g each immune egg product is added to a one dose packet. In another aspect, 1 to 5 g, 2 g to 4 g, 1.5 g, 2.0 g, 2.5 g, 3.0 g, 3.5 g, 4.0 g, 4.5 g or 5 g dried colostrum is added to the same packet.

Prior to use, the contents of the packet, or sachet, are mixed into approximately 2 ounces of purified water, or some other oral liquid. The entire reconstituted formulation is administered orally to the subject. The composition can be administered one to four times per day for two to ten days. In a specific embodiment, the composition is administered once per day for 3 consecutive days. The disclosure provides a method of treating undifferentiated pediatric diarrhea, by administration of the composition of the disclosure once per day for two, three or four days.

In one aspect, the composition of the disclosure is administered as an adjunct therapy to antibiotic treatment. In this aspect, the composition may be administered once per day for the first three days of treatment. In another aspect, the composition of the disclosure is administered with oral rehydration solution (ORS). In another aspect, the composition of the disclosure is co-administered with an oral zinc formulation. In another aspect, the composition of the disclosure is administered as an adjunct to antibiotic treatment to prevent overgrowth of a particular pathogenic organism that is resistant to the antibiotic. As described in detail in the examples, the composition and method is effective to rapidly resolve the symptoms of undifferentiated pediatric diarrhea, resulting in significantly decreased stool volume, stool frequency and duration of diarrhea, as well as significantly improved physician reported well-being.

In one alternative embodiment, the compositions of the disclosure are used to treat traveler's diarrhea. The onset of TD usually occurs within the first week of travel but may occur at any time while traveling, and even after returning home. The most important determinant of risk is the traveler's destination. High-risk destinations are the developing countries of Latin America, Africa, the Middle East, and Asia. Persons at particular high-risk include young adults, immunosuppressed persons, persons with inflammatory-bowel disease or diabetes, and persons taking H-2 blockers or antacids. Most TD cases begin abruptly. The illness usually results in increased frequency, volume, and weight of stool. Altered stool consistency also is common. Typically, a traveler experiences four to five loose or watery bowel movements each day. Other commonly associated symptoms are nausea, vomiting, diarrhea, abdominal cramping, bloating, fever, urgency, and malaise.

Infectious agents are the primary cause of TD. Bacterial enteropathogens cause approximately 80% of TD cases. The most common causative agent isolated in countries surveyed has been enterotoxigenic *Escherichia coli* (ETEC). ETEC produce watery diarrhea with associated cramps and low-grade or no fever. Besides ETEC and other bacterial pathogens, a variety of viral and parasitic enteric pathogens also are potential causative agents.

In one aspect, the composition of the disclosure is administered to the subject once per day for three consecutive days as an alternative or adjunct to antibiotic treatment of traveler's diarrhea. Limited field study evidence suggests improvement in diarrheal symptoms within 24 or 48 hours of the first dose. Alternatively, two doses per day of the composition of the disclosure are administered on day 1, followed by a single dose on days 2 and 3. In one aspect, the composition of the disclosure is administered on an alternate daily or weekly schedule, or on a reduced dosage schedule to for prophylaxis of traveler's diarrhea.

In another alternative embodiment, the compositions of the disclosure are used to as a "prebiotic" for gastrointestinal flora management of a subject, for example, prior to administration of a probiotic. As used herein, the term "prebiotic" refers to a composition that allows specific changes, both in the composition and/or the activity of the gastrointestinal microflora that confers benefits upon the subject's well-being and health. In one aspect, the composition is useful to manage gastrointestinal flora so as to reduce or eliminate one or more undesirable strains of bacteria. In one aspect, the anti-antigenic immunoglobulin composition is tailored to manage gastrointestinal flora so as to reduce or eliminate one or more undesirable strains of bacteria. In another aspect, the compositions are used as an adjunct to traditional prebiotics. In a further aspect, the composition of the disclosure further comprises a soluble fiber. In a further aspect the composition is used alone for flora management.

In another aspect, the disclosure provides a method of gastrointestinal flora management in a subject comprising the steps of administering the composition of the disclosure to reduce or eliminate one or more undesirable strains of bacteria, followed by administering a probiotic to introduce one or more desirable strains of bacteria. In another aspect, the composition of the disclosure is administered as an adjunct to antibiotic treatment to prevent overgrowth of a particular pathogenic organism that is resistant to the antibiotic.

Example 1. Compositions for the Treatment of Diarrhea

Diarrhea is a symptom of a broad range of causes including bacterial, viral, protozoal and parasitic infections. Bacterial diarrhea is induced by multiple organisms, including various forms of *Escherichia coli, Salmonella, Vibrio cholerae* and *parahemolyticus, Shigella, Campylobacter, Yersinia* and others. Viral pediatric diarrhea is often caused by Rotavirus, but also may be caused by several other viruses.

There are known to be multiple causative organisms in diarrhea. These causative organisms can be organized into common clusters that produce structurally related toxins, to which a series of broad-spectrum neutralizing antibodies can be created that, when admixed into a formulation with clinically effective titers, can be used as a broad-spectrum organism-independent therapeutic intervention for toxin-mediated diarrhea.

Briefly, antibodies specific to causative organisms of diarrhea are generated by inoculation of chickens with antigen. Immune eggs are collected and whole egg is pasteurized and spray dried to obtain a powderized form. Commercial bovine colostrum is mixed in a powderized form. The two powders are added sequentially to a single dose packet and sealed, and distributed in dried form for an oral formulation. Before administration, the powdered oral formulation is mixed with a small quantity of water prior to oral consumption.

This treatment confers passive immunity to patients, as demonstrated in the Examples herein. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative medicines.

Example 1A

Chickens were individually inoculated with purified antigens derived from 5 *E. coli* strains: four ATCC strains, containing *E. coli* adherence pili antigens F41, 97P, F19 and K99, and one wild type *E. coli* strain derived from milk. Each chicken was inoculated with only one antigen. Chickens were inoculated once per week for three weeks. Freund's adjuvant was employed for the first inoculation, followed by Freund's incomplete adjuvant for the second and third inoculations. Two shots, left and right breast were used per inoculation. Eggs were housed separately; eggs were collected, flash pasteurized and spray dried. Each of the five antibody preparations were mixed in equal parts. The dried egg powder anti *E. coli* antibody preparation was stored frozen for about 2 years.

A second flock of chickens was inoculated with a mixed antigen preparation containing rotavirus, coronavirus and *E. coli* antigens. The same inoculation, collection and egg processing protocols were employed as above. The dried egg powder anti-scours antibody preparation was stored frozen for 1.5 years. ELISA was used to characterize the antibody preparations.

One gram each of the dried anti-*E. coli* antibody preparation and the dried anti-scours antibody preparation were added with 3 grams or 4 grams of commercial dried full-fat bovine colostrum in a single dose packet.

Example 1B

Three flocks of chickens were individually inoculated with one each of different mixerd antigen preparations: a first antigen preparation containing rotavirus (serotypes G6 and G10), coronavirus, enterotoxigenic *E. coli* stains with K99 pili adherence factor, and *Clostridium perfringens* type C toxoid with adjuvant); a second preparation containing enterotoxigenic strains of *E. coli* having K99, K88, 987P or F41 adherence factors); and a third mixed antigen preparation containing various *E. coli* endotoxin; with adjuvant). Each of three flocks only received a single mixed antigen preparation. Eggs were collected, cleaned, broken, pasteurized and spray dried or thermal dried to create three dried immune egg products. Dried egg product was optionally evaluated by ELISA for specific IgY activity. An equal weight of each of the three dried immune egg products was combined with 3 g or 4 g of dried colostrum in a single dose packet. Either 2 g, 3 g, or 4 g of combined weight of dried immune egg product was employed per single dose packet, as described below. In one aspect, the commercial dried colostrum did not exhibit specific activity toward the antigens of the vaccines.

Example 1C. Immunization of Chickens for IgY Production

The following immunization protocol was adapted from a *Gallus* Immunotech, Inc. protocol and can be utilized for generation of IgY polyclonal antibodies. A few eggs are optionally collected prior to immunization to serve as a baseline control. If a mixed antigen preparation for cattle or hogs is employed, it is diluted at 1:2, 1:4, 1:8, or 1:16 prior to administration. On day 0, chickens are injected with between 0.02 and 0.5 mg antigen with Freund's complete adjuvant. Injections can be either subcutaneous or intramuscularly into the breast tissue of the hen at multiple sites. The total volume of antigen/adjuvant mixture can be about 1 mL with adjuvant from one-half to two-thirds of the volume. Immunizations are repeated, typically, on days 14, 21 and 28, using Freund's incomplete adjuvant, with about half the initial amount of antigen. Typically, specific antibody can be detected at about day 30 in eggs. For prolonged antibody production, hens are boosted every couple of months. Eggs can be stored in cold storage prior to processing and/or purification of IgY. In one aspect, eggs can be held in cold storage for up to one month, or up to two months, prior to processing or purification. In another aspect, IgY can be generated in a similar fashion in duck, goose, ostrich, quail, or turkey eggs, with use of appropriate amounts of antigen.

Example 2. Ingested Antibody Treatment for *Clostridium difficile*

In one embodiment, the invention methods and compositions are used to treat *Clostridium difficile* (*C. difficile*), a bacterium that is naturally present in most people. The population levels of *C. difficile* are kept under control by the other natural flora of the bowel. Patients often develop *C. difficile* infections when antibiotics administered for another medical condition deplete the natural flora of the bowel, allowing *C. difficile* populations to multiply unchecked. While many strains of *C. difficile* can be treated by specialized antibiotics an increasingly large number of *C. difficile* strains are resistant to antibiotic treatment. This leads to a lengthy and difficult recovery for patients, and may even become life-threatening in certain circumstances. A process neutralizing *C. difficile* populations with an ingested antibody that confers passive immunity is capable of controlling *C. difficile* population levels to allow a natural bowel flora balance to be restored.

As is the case in anti-diarrhea formulations caused by rotavirus and gram-negative bacteria, an antibody embedded in a carrier matrix formulated specifically to bind to *C. difficile* or its toxins is an effective therapeutic approach. This formulation can be used to either treat an ongoing infection, or to prevent such an infection from occurring. Therefore, the treatment can be administered alone, or concurrently with an antibiotic. This treatment not only benefits patients recovering from a *C. difficile* episode, but can be administered to patients at high risk of developing *C. difficile* as a prophylactic.

The antibodies that neutralize *C. difficile* are ingested in a carrier matrix (a mixture of proteins and enzymes that are intended to "activate" the antibody in the bowel, as well as provide useful secondary immunity, protection or nutrition). In one embodiment, the antibodies are produced by injecting, or inoculating, an animal with an antigen, or a combination of antigens, which may or may not be contained in a mixed antigen preparation, (potentially combined with an adjuvant to elicit a stronger immune response).

In one aspect, the antigen is obtained from, or derived from, a *C. difficile* antigen or toxin. In another aspect, the combination of antigens contains one of more antigens or toxins derived from *C. difficile*, and one or more additional viral antigens. In another aspect, the combination of antigens contains one or more antigens or toxins derived from *C. difficile*, and one or more additional bacterial antigens or toxins. In another aspect, the combination of antigens contains one or more antigens derived from *C. difficile*, and one or more additional protozoal antigens. In another aspect, the combination of antigens contains one or more antigens derived from *C. difficile*, and one or more additional fungal antigens.

The antibodies are then either obtained from, isolated from, or derived from, an animal product, such as milk, eggs, or colostrum from the animal or harvested directly from, the animal, e.g. serum, plasma. In a particular aspect, hens are inoculated with the antigen, combination of antigens, or vaccine, and the antibodies are obtained from whole eggs, or egg yolks, or derived from, or purified from whole eggs or egg yolks of the inoculated chickens. In another aspect, the antibodies are polyclonal antibodies.

This composition is intended to help treat *C. difficile* infections, or be a prophylactic against *C. difficile* infection. For example, the substance is comprised of antibodies targeted specifically to *C. difficile*, embedded within a carrier matrix (for example, colostrum). After harvesting, the antibodies may be powderized. The carrier matrix may also be powderized. The two powders may then be mixed thoroughly, or added separately to a single dose packet, or vial, and distributed in dried form. In a preferred method of administration, the substance will be administered orally, by ingestion. To consume, the powdered substance will be mixed with a small quantity of a liquid, such as water, milk, juice, or electrolyte solution, immediately prior to consumption, and will be taken as directed by a physician. Other methods of delivery are also contemplated.

Current treatment for *C. difficile* infection focuses on antibiotic therapy. However, in cases where strong antibiotics were the cause of infection, and in cases where resistance to antibiotics has been developed, few alternative treatments are currently available. The present embodiment seeks to neutralize *C. difficile* by utilizing natural immune mechanisms, rather than toxic antibiotics. It has the advantage of allowing the growth of naturally occurring flora in the bowel while reducing *C. difficile* population levels.

The combination of antibodies embedded within a carrier matrix to enhance the effectiveness of the antibodies is not currently used by any *C. difficile* disease treatment. The invention methods confer passive immunity to patients. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative medicines.

In one aspect, selected antibodies are obtained, purified and isolated and prepared in a powderized form. In another aspect, the selected antibodies are not purified, or isolated, but processed as a whole product. For example, the contents of the whole egg obtained from the inoculated chicken is processed, e.g. pasteurized, and prepared in a powderized form, without additional purification steps. An activating enzyme/protein mixture (for example, including colostrum) is also prepared in a powderized form. The two powders are mixed thoroughly and distributed in dried form for an oral formulation. Before administration, the powdered oral formulation is mixed with a small quantity of water prior to consumption.

This treatment confers passive immunity to patients. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative medicines.

Example 3. Ingested Antibody Treatment for *Helicobacter avlori*

*Helicobacter pylori* (*H. pylori*) is a gram-negative bacterium which can inhabit areas of the stomach. It is generally believed that *H. pylori* is associated duodenal and gastric ulcers and possibly stomach cancer. *H. pylori* can escape the acidic environment of the stomach lumen by burrowing into the mucus layer of the epithelial cell surface which has a more neutral pH environment. *H. pylori* can produce adhesins for binding to membrane associated lipids or carbohydrates of epithelial cells. Colonization of *H. pylori* inside areas of the stomach can results in chronic gastritis, a long-lasting inflammation of the stomach. A major cause of peptic ulcer is *H. pylori* infection.

Selected antibodies against *Helicobacter pylori* are obtained and prepared in a powderized form. An activating enzyme/protein mixture (for example, including colostrum) is also prepared in a powderized form. The two powders are mixed thoroughly, or added separately to single dose packets or vials, and distributed in dried form for an oral formulation. Before administration, the powdered oral formulation is mixed with a small quantity of water prior to consumption.

This treatment confers passive immunity to patients. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative medicines.

Example 4. Clinical Studies—Efficacy in Undifferentiated Diarrhea

Effective broad-spectrum treatment of diarrhea is a significant challenge due to the wide range of causative organisms, the limited availability of diagnostic testing for directing treatment regimes. Current standard intervention for cases of severe diarrhea includes ubiquitous administration of antibiotics and oral rehydration salts (ORS). However, this approach has shown limited effectiveness, and has promoted the development of antibiotic resistant bacteria strains.

Example 4A. Field Study (Trial)s 1 and 2

Clinical studies were performed to evaluate the tolerability and efficacy of the formulation of Example 1A in treating, or accelerating the resolution of undifferentiated diarrhea. A first open, single-center, non-comparative study enrolled a total of 63 pediatric patients with pediatric diarrhea of both genders between six months and five years of age. The study compared clinical outcomes of Test Group A, "Trial 1", receiving the oral formulation of Example 1A, administered with antibiotic and ORS, to a Control Group B, receiving only antibiotic and ORS. A second Test Group AA, "Trial 2", enrolled 33 patients in a follow up study to test the formulation of Example 1A under different seasonal conditions.

All participating pediatric patients presented a "serious" or "severe" diarrhea profile (level 4 or 5) on a 5 point scale (see Table 1), as assessed by attending physician. No diagnostic differentiation was made as to causative agent or etiology of the pediatric diarrhea. Patients with rice water stool of bloody stool were excluded. Additionally, patients with known allergies to milk, chicken, or egg products were excluded.

TABLE 1

| The 5-point scale | | |
| --- | --- | --- |
| | Level 1 | Level 5 |
| Stool Frequency | 1-2 per day | 10 or more per day |
| Stool Consistency | 1 = normal | 5 = fully liquid |
| Physician Assessed Well-being | 1 = normal | 5 = severe (typically inpatient) |

Enrolled children (n=63) were divided into two groups, an experimental group Study 1, "Group A" (34 enrolled children; 29 completing trial), negative control "Group B", (29 enrolled children; 28 completing trial), and Study 2 "Group AA" (31 enrolled). A second control group "Group BB" receiving antibiotic and ORS was used as a negative control concurrently with the Group AA, however, the results are omitted from the figures.

Each test group received 2 g combined egg powder and 4 g colostrum, mixed in water, administered orally once per day for three consecutive days. Each group was observed and the data are collected for five days. Group A received the composition from Example 1 in addition to a standard regiment of antibiotics and oral rehydration supplements (ORS), as determined by the attending pediatrician. Group B is treated with a standard regimen of antibiotics and ORS. A six month window of time between Study 1 and Study 2 was allowed elapse in order to test seasonality. Both trials were conducted in the same study center. In each group, antibiotic and ORS prescriptions were determined on a case-by-case basis by the attending pediatrician (Table 2).

TABLE 2

Study Groups with Numbers of Cases Completed

| Group | Therapy administered | Completed | Treatment Period | Observation |
|---|---|---|---|---|
| A | Composition from Example 1 + antibiotic + ORS | 29 | Composition from Example 1: days 1-4 Antibiotic + ORS: days 1-6 | 5 days |
| AA | Composition from Example 1 + Antibiotic + ORS | 31 | Composition from Example 1: days 1-3 Antibiotic + ORS: days 1-6 | 5 days |
| B | Antibiotic + ORS | 28 | Antibiotic + ORS: days 1-5 | 5 days |

The composition from Example 1A was packaged in 5 gram powder single dose sachets. The composition was administered orally, with one packet re-suspended in approximately 2 ounces of drinking water. Patients were required to drink the entire suspension in one setting, immediately after re-suspension was complete, and this protocol was followed in all cases.

Parameters covered in this example, as measured for each patient, included stool frequency, stool consistency, and physician assessed well-being. Stool frequency is the guardian or hospital reported number of diarrheal bowel movements per 24 hour period. Stool consistency is a 1-5 scale of consistency with 1 indicating normal and 5 indicating liquid. Physician assessed well-being is a 1-5 scale of overall condition with 1 indicating normal parameters for a healthy child and 5 indicating a severely ill child.

Physicians participating in the trial were asked to provide their experience of the typically patient progression, as measured by the three parameters described, over the course of six days. The reported values were aggregated into a single expected patient progression baseline for each parameter. Patients were evaluated both in terms of improvement relative to expected outcomes based on doctor experience, and against the concurrent negative controls.

Data analysis was conducted with MS Excel and Matlab. Statistical significance was computed by a Chi-square test with p-value of <0.05 considered significant. Results are shown in FIGS. 1 to 3.

Dramatic improvements in patients receiving the composition from Example 1A were observed within 24 hours of the initial dose administration. Within 48 hours after initial dose administration patients were generally stabilized at normal or near normal levels.

As shown in FIG. 1, average number of diarrheal bowel movements in a 24 hour period decreased from 9 to 2 in Group A (Trial 1) after the initial dose of the composition from Example 1. Group AA (Trial 2) exhibited a similar reduction from 10 to 3. In contrast, average number of episodes in Group B (Negative control) decreased from 11 to 10 in the same time period. The average number of episodes in Groups A and AA (Trials 1 and 2) remained constant at 2 from day 3 onward, while Group B diminished gradually eventually exhibiting 6 episodes per 24 hours by day five. In Group A, within 24 hours of the treatment with the composition from Example 1, stool frequency rates returned to near normal levels, 2.32±2.48, an over 86% reduction in the duration of gastroenteric symptoms when compared to the control population (P<0.001). Within 48 hours stool frequency rates improve to 2.14±2.19. In Group AA, frequency rates showed similar stabilization rates, improving to 2.56+/−0.68 within 24 hours and 2.00+/−0.45 within 48 hours, a marked improvement compared to control (P<0.001)

Figure 2:
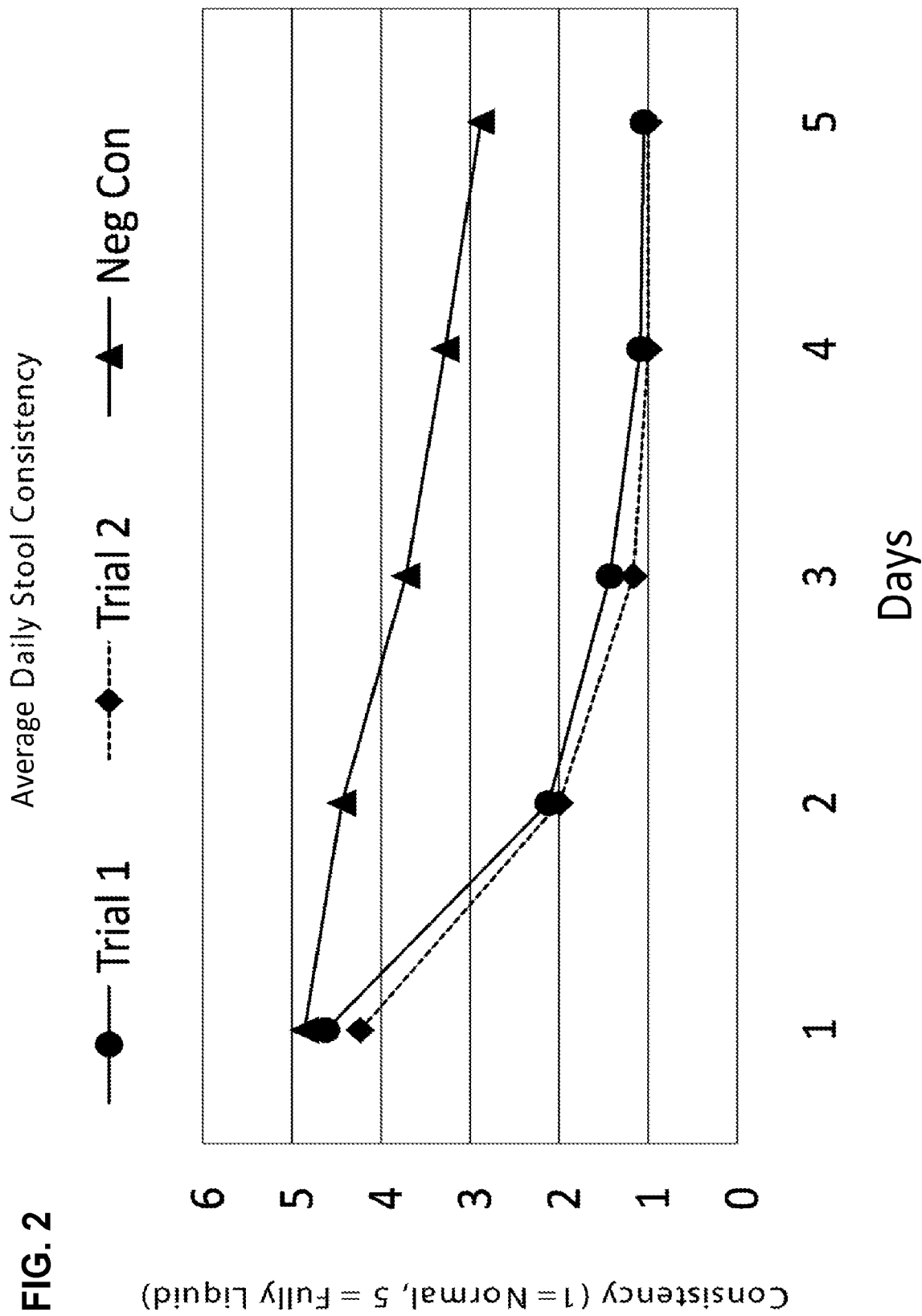
Figure 3:
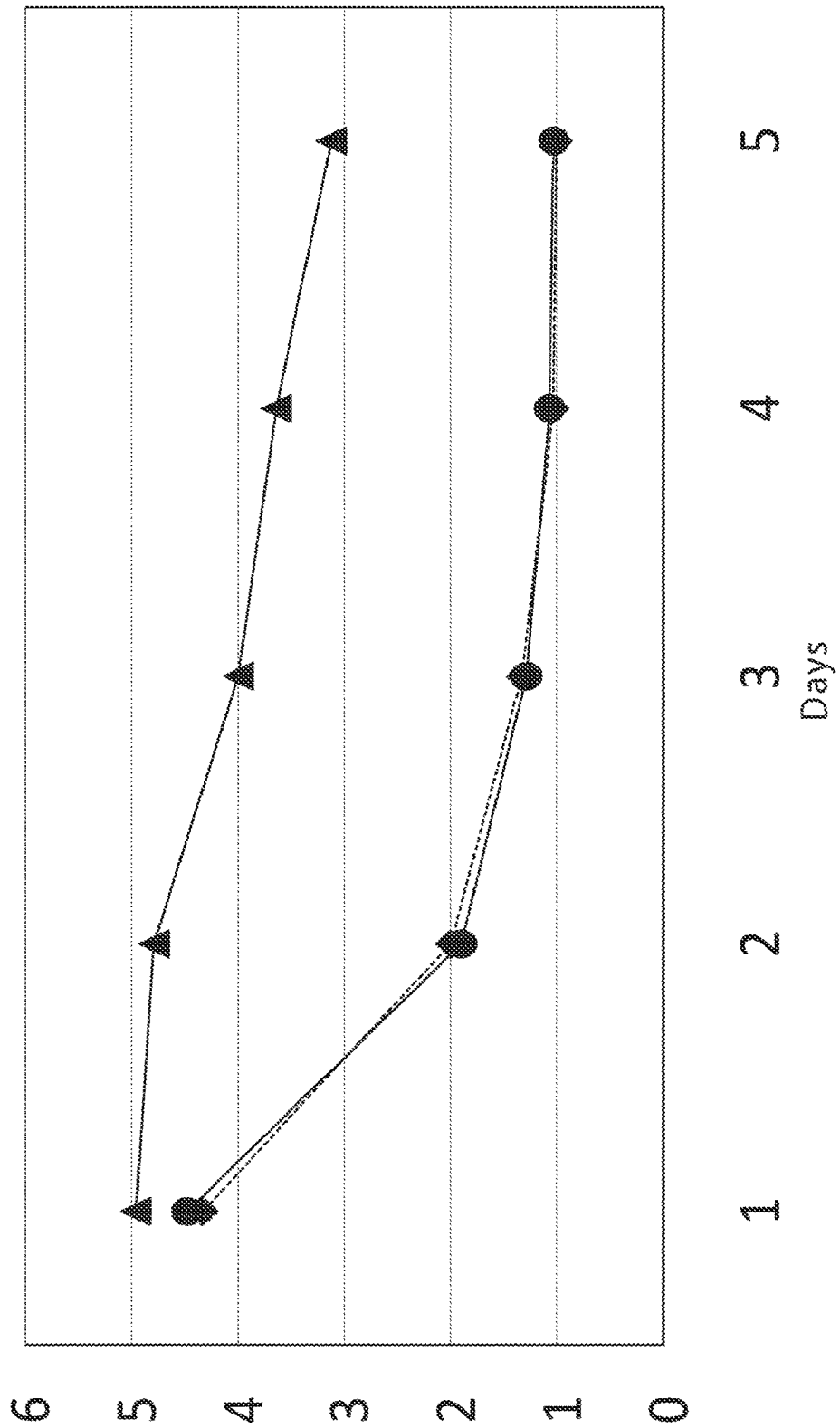
Figure 4:
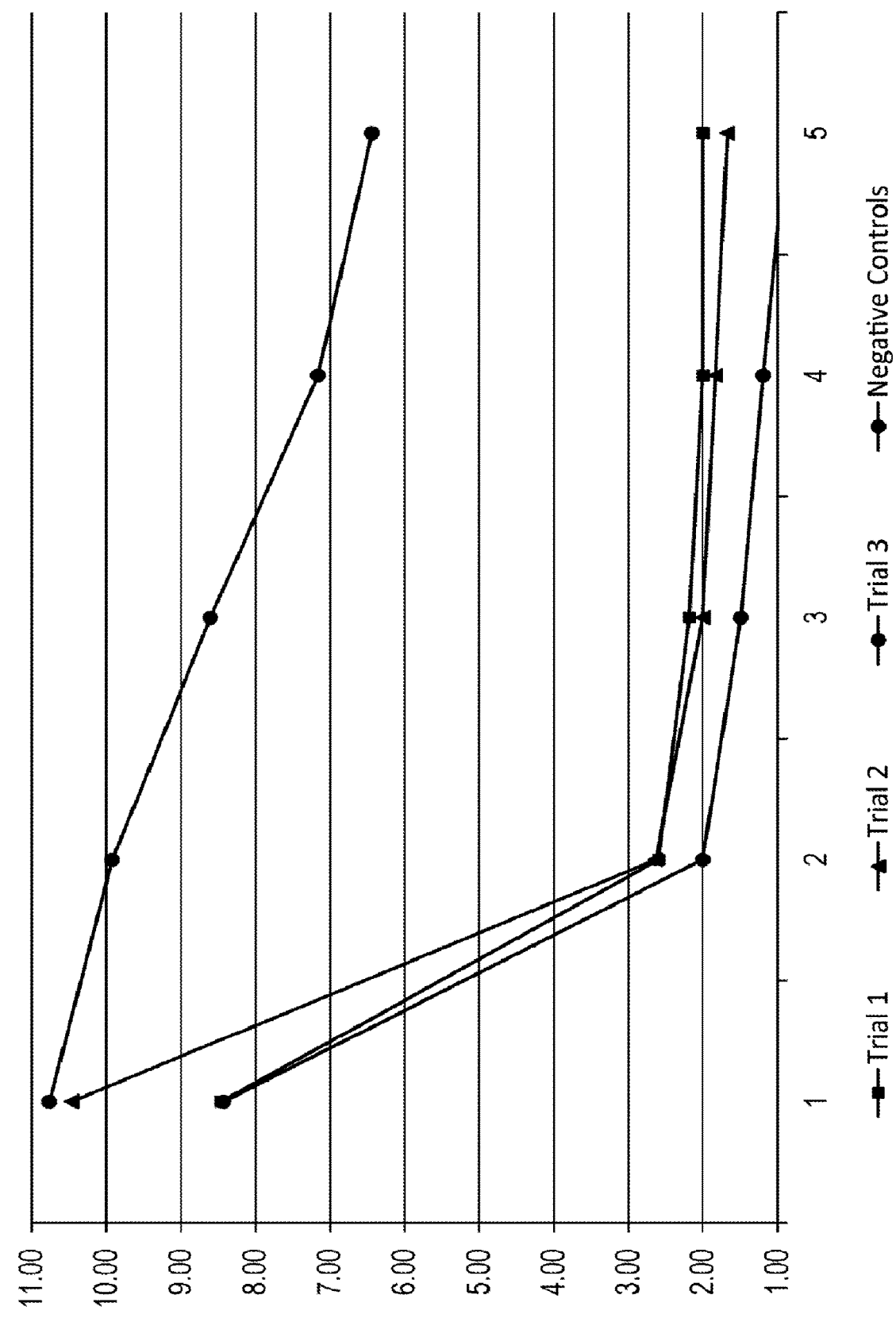
Figure 5:
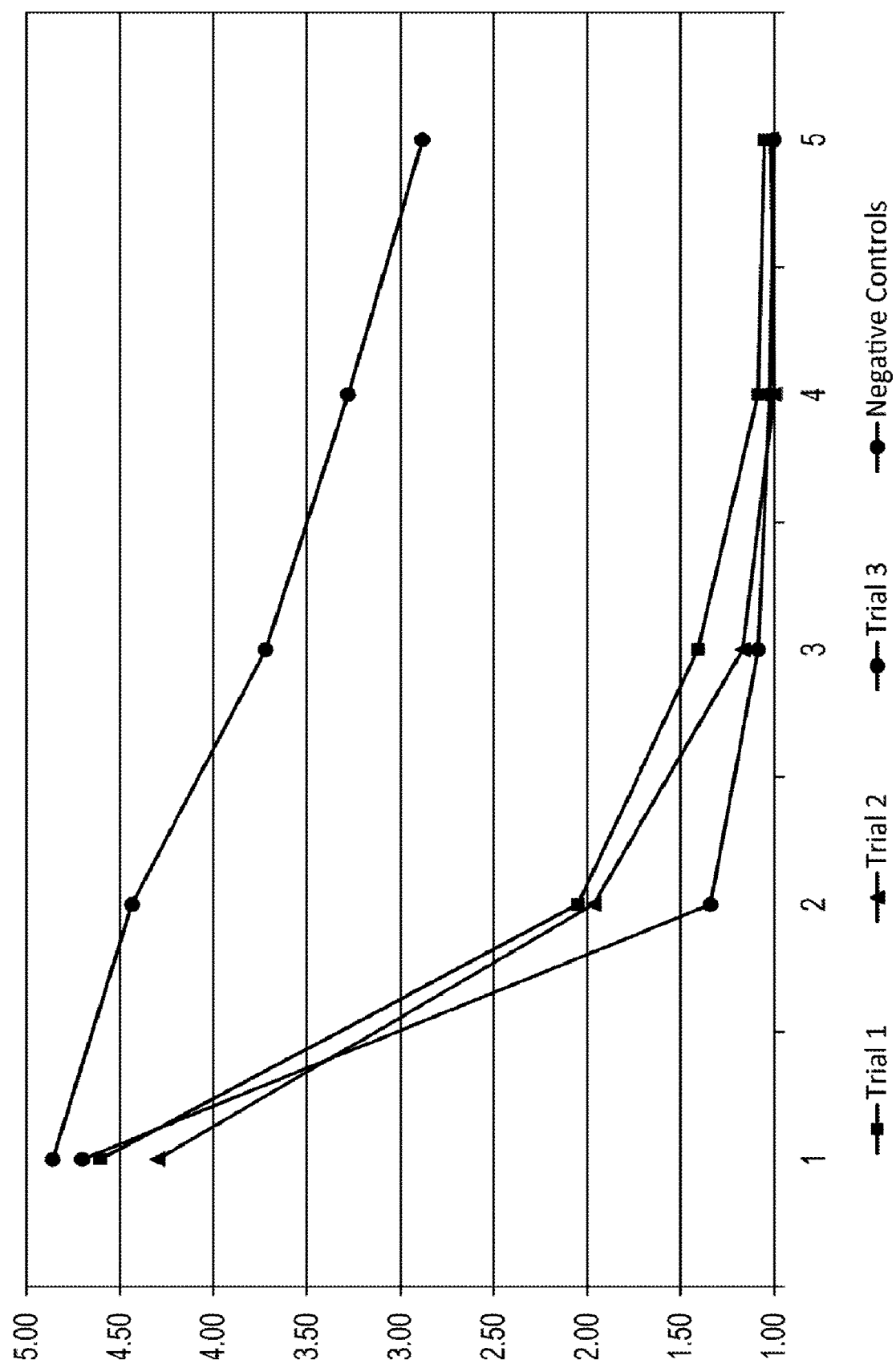
Figure 6:
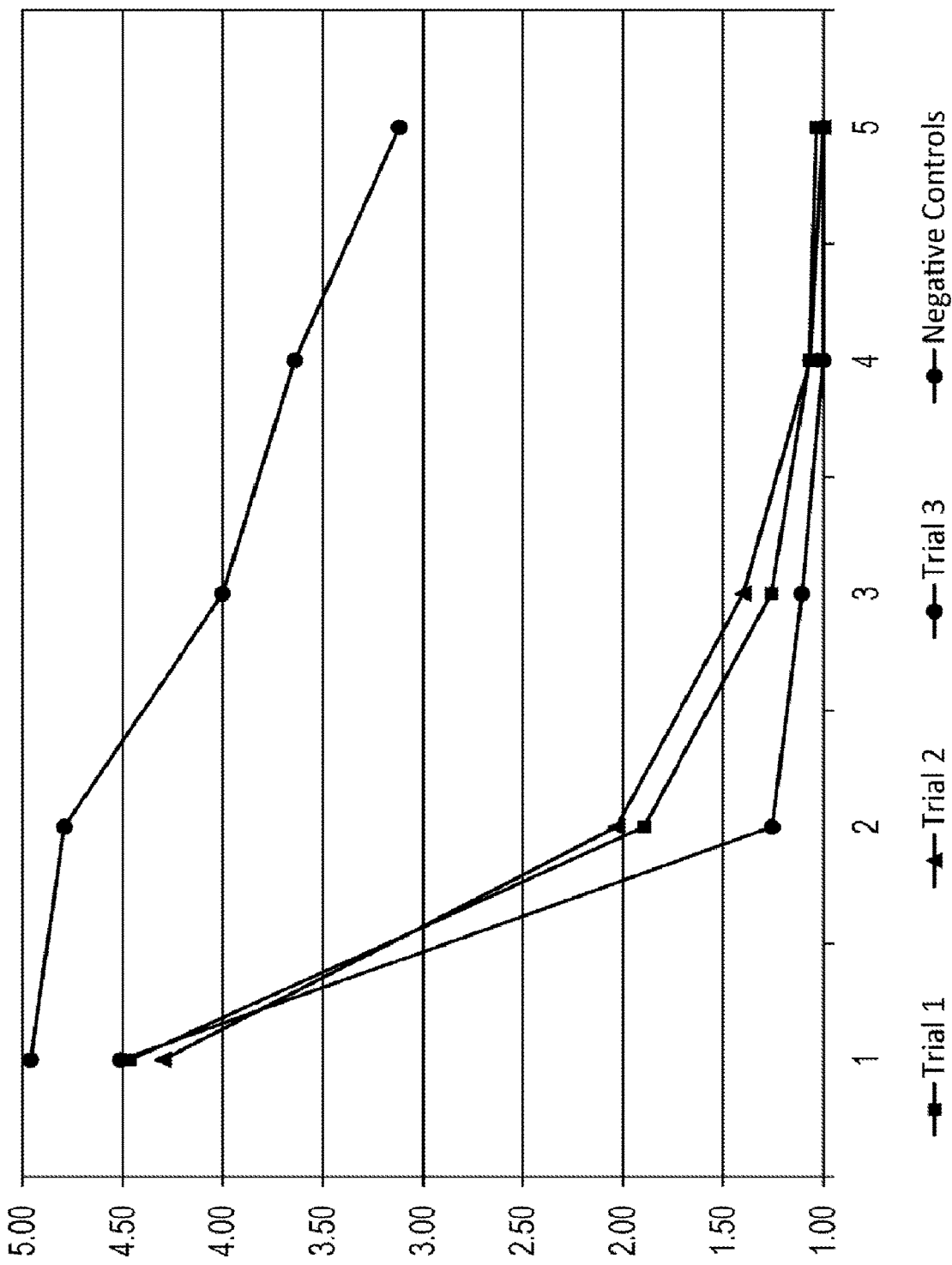
Figure 7:
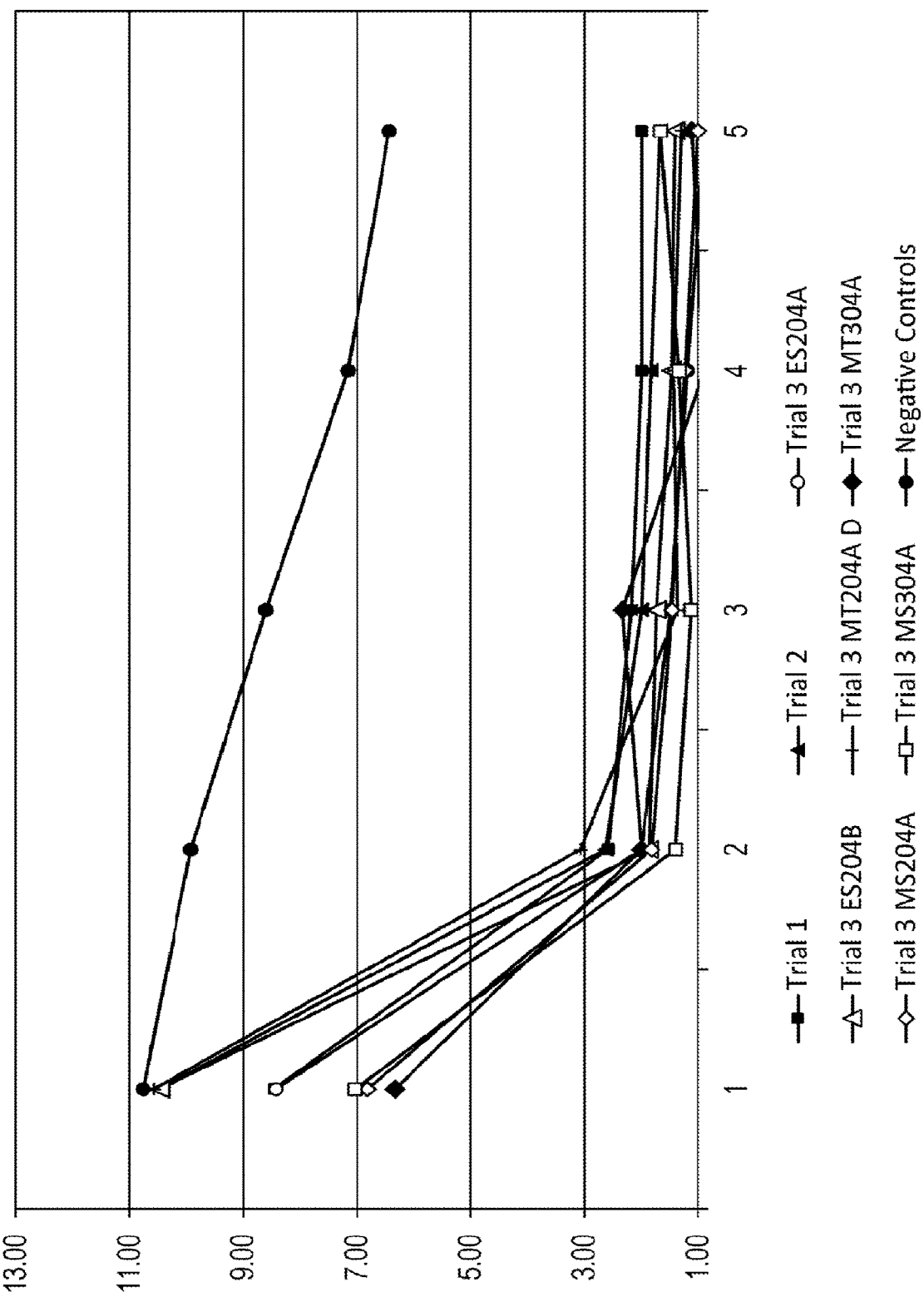
Figure 8:
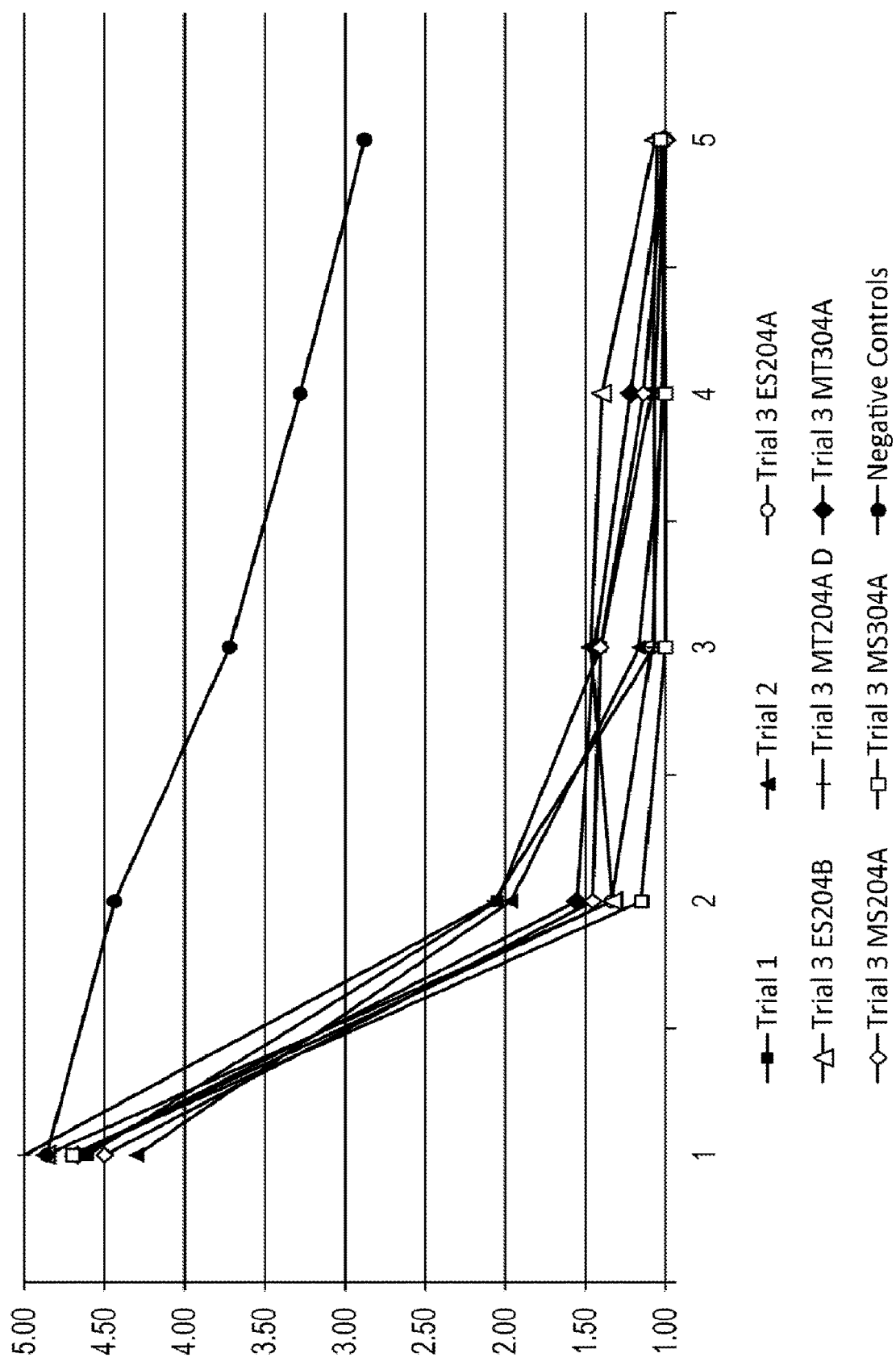
Figure 9:
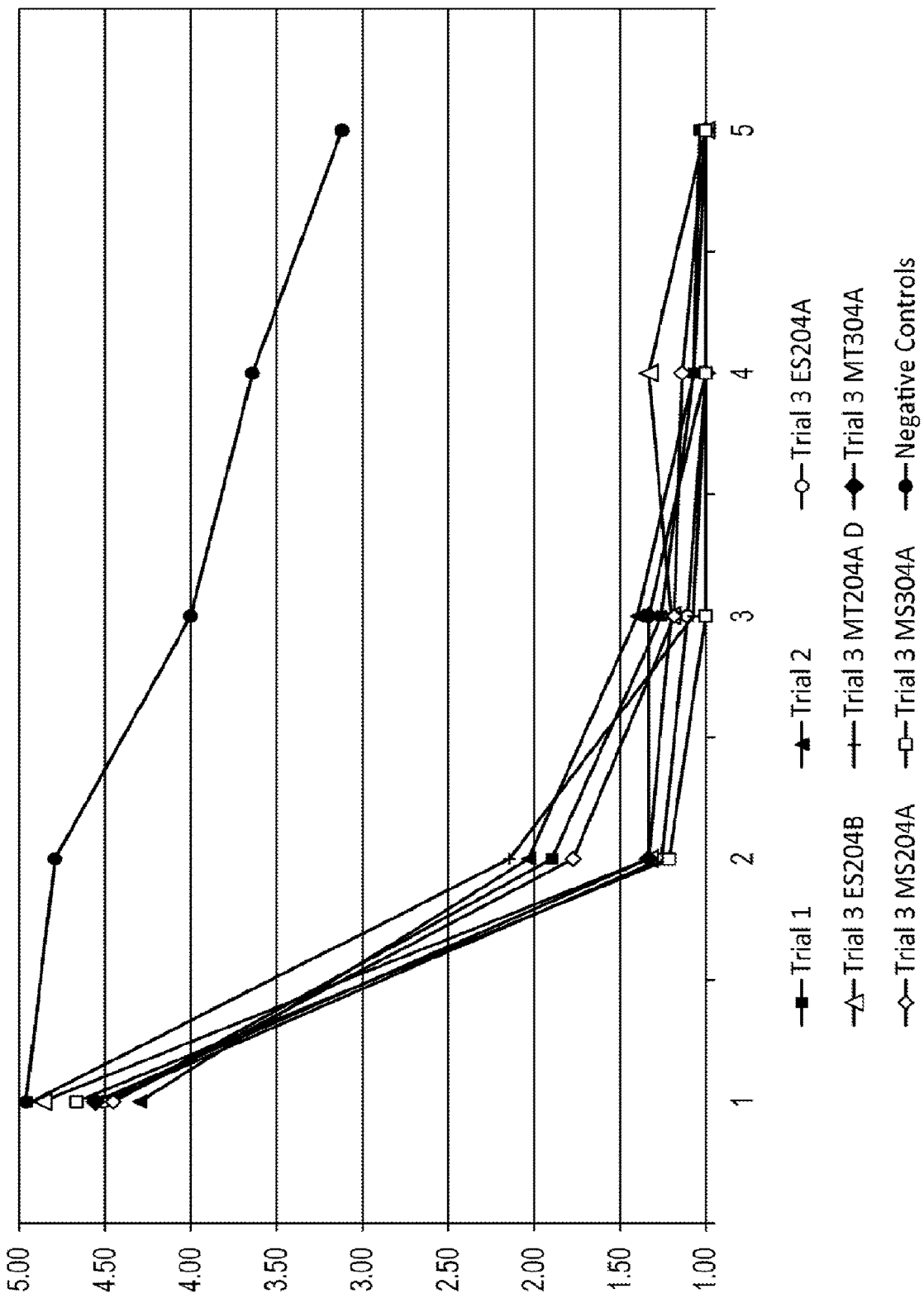

As shown in FIG. 2, initial stool consistency was liquid in all patients. Group A and Group AA stool consistency improved to near-normal levels in 24 hours, after the first dose of the composition, after the first dose of the composition from Example 1. Control Group B consistency improved but was still liquid in 24 hours, with symptoms not fully resolving the entire observation period. Group A obtained normal stool consistency in 48 hours and for the remainder of the study, while Group B, by day 3, improved to mostly liquid. Group B eventually reached near-normal levels of stool consistency by day 6, while Group A stool consistency remained normal throughout days 3-6.

Surprisingly, within 24 hours of the treatment with the composition from Example 1A, stool consistency rates returned to mild levels, 2.05±1.02 for Group A and 1.96+/−0.61 for Group AA, an over 86% reduction in the duration of gastroenteric symptoms when compared to the control population (P<0.001). Within 48 hours, Group A stool consistency dropped further to near normal levels 1.41±0.9, and Group AA levels were 1.17+/−0.37.

As shown in FIG. 3, all patients enrolled in the study were rated as severely ill by attending physicians, up to and including serious dehydration, vomiting and low responsiveness. Patients in Group A and Group AA improved significantly overnight (P<0.001), after the first dose of the composition from Example 1, to an average well-being assessment level of approximately two. At 24 hours, Group B patients remained severely ill. Group A and Group AA patients, at 48 hours, improved to near normal and continued to improve on day three obtaining normal condition, while Group B patients improved but remained very ill. Throughout days 4-6, patients in Group A remain fully recovered while patients in Group B improved in a linear manner; however they remained moderately ill at the end of the study.

Overall physician reported well-being retuned to near healthy level within one day, with Group A dropping from an initial value of 4.46±0.5 1 to 1.9±0.9, a level considered within normal parameters for this population. Group AA displayed similar results, falling from an initial level of 4.3+/−0.46 to 2.03+/−0.49. This collectively represents an 86% reduction in the duration of illness when compared the control population (p<0.001). Within 48 hours, physician reported well-being improved further to 1.26±0.83 in Group A and 1.4+/−0.49 for Group AA.

A check to confirm the normal distribution of trial cases against expected prevalence of Rotavirus was made within Group A (Trial 1), independent of the primary trial evaluation. Stool samples were collected for 26 of the 29 experimental patients in Group A and 24 of the 31 patients from Group AA, and were tested at an independent reference lab using an established commercial agglutination assay (Slidex Rota-kit, bioMerieux, France). Seven of the 26 patients sampled in Group A test positive for Rotavirus (27% of the tested population). This pediatric Rotavirus infection prevalence is in line with expected results for the season and the degree of severity of diarrhea cases admitted to the study. Four of the 24 tested positive in Group AA (17% of the tested population). The prevalence of rotavirus fro Group AA was somewhat lower than expected. Therefore, the composition of Example 1A was deemed effective as administered to treat undifferentiated diarrhea, including that caused by rotavirus infection.

To further determine the similarity of response to the composition from Example 1 between the Rotavirus positive group (RV) and the non-Rotavirus positive group (Non-RV), the Pearson's Product-Moment Correlation Coefficient was used (represented as "R), the strength of which is represented in the range −1 to 1. Calculation of R used the average of the Non-RV and RV group for each time point, with calculation of the R-value from the average value of each group over the 6 days.

The R value of the RV group's association with the Non-RV group for the Physician Assessed Well-being dataset is 0.99029, showing a very strong linear dependence and covariance between the two groups. The behaviors of Non-RV and RV patients are strongly predictive of each other, and showed very similar responses to the treatment over the six day treatment and observation period. These results confirm the efficacy of the composition from Example 1 in Rotavirus mediated diarrhea cases (Table 3).

TABLE 3

RV/Non-RV Average Values

| Day | RV | Non-RV |
|---|---|---|
| 1 | 4.71 | 4.38 |
| 2 | 1.71 | 1.95 |
| 3 | 1.33 | 1.24 |
| 4 | 1.28 | 1 |
| 5 | 1.14 | 1 |
| 6 | 1 | 1 |

Of the 96 patients enrolled in the studies, 88 completed the full six day study period. Four patients were withdrawn from Group A, and two from Group AA by the physician when it was determined that their enteritis was co-morbid with, or the result of, other conditions; as shown in Table 4. One patient from Group A was lost to the trial when his guardian decided that the patient was well enough to withdraw after the second dose of the composition from Example 1. And, one patient was withdrawn from Group B due to record keeping error (Table 4).

TABLE 4

Patients Withdrawn from Study

| Patient # | Group | Reason | Withdrawn by |
|---|---|---|---|
| A 12 | Experimental (A) | Measles | Study doctor |
| A 19 | Experimental (A) | Meningitis | 1 |
| A26 | Experimental (A) | Patient deemed well | Guardian |
| A28 | Experimental (A) | Measles | Study doctor |
| A33 | Experimental (A) | Meningitis | Study doctor |
| B08 | Control (B) | Record keeping error | Study doctor |

These results suggest that the composition from Example 1 may provide a safe and effective treatment for undifferentiated pediatric diarrhea. Reducing the duration and severity of diarrhea will prevent a significant amount of morbidity and mortality associated with pediatric diarrhea and may also help prevent diarrhea-associated co-morbidities from developing in pediatric patients.

After one day of the treatment with the composition from Example 1, pediatricians report substantial improvement in overall well-being in 100% of the patients completing the trial. Surprisingly, significant reduction in both the duration and severity of illness provided an 86% reduction in length of diarrhea episode after two days of the treatment with the composition from Example 1. Independent Rotavirus testing confirmed efficacy of the composition from Example 1A in these cases.

The composition from Example 1A was shown to be highly effective in the treatment of undifferentiated diarrhea, greatly reducing the length and severity of illness when compared to conventional therapies alone. The composition from Example 1A is well-tolerated with no adverse side-effects reported. The results of this study represent an important and robust improvement in the treatment of pediatric diarrhea within demanding field environments. These results provide an opportunity for additionally investigation of the mechanisms and biochemistry by which the composition of the invention protects patients from the most severe symptoms of undifferentiated diarrhea.

Example 4B. Field Study (Trial) 3

A third study trial was conducted with 140 treated patients and 30 negative control patients enrolled in Trial 3. The daily dose of the composition in the treated arm contained either 2 g total of equal portions of dried whole egg from each of three flocks, each inoculated separately with one commercial scours or mastitis vaccine; and 4 grams of dried bovine colostrum (ES204A; MS204A); or 3 grams of equal portions by weight of dried whole egg from each of three flocks, each inoculated separately with one commercial scours or mastitis vaccine and four grams of dried bovine colostrum (MS304A). In addition, egg was processed either by spray drying (S) or thermal drying (T). The flocks were housed at two different geographic locations within the United States (M) or (E).

Trial 3 was conducted as described above; patients were treated with the compositions once per day, for three consecutive days. Average results for Trial 3 compared to Trials 1 and 2 are shown in FIGS. 4-9. A small arm of Trial 3 with 15 patients was treated with 2 g dried egg and 4 g colostrum once per day for two days and exhibited significant improvement at days one and two in each measured parameter. This group exhibited a slight average relapse effect in symptom scoring in physician reported well-being on day 4, stool consistency on days 3 and 4 (ES204B). However, these values were still significantly improved compared to the negative control group.

These results show that a solid formulation for suspension comprising specific binding molecules which are antigen-specific IgY antibodies in whole dried egg and a carrier matrix, which is non-immune dried bovine colostrum is economical and effective. The matrix of the disclosure, dried bovine colostrum, is easily commercially available and can provide higher levels of various matrix components than milk. This is in contrast to, for example, the prior art teachings of Larrson et al, US 2010/0233162. Larsson provides a method for local administration of isolated chicken yolk immune globulins (IgY) in human breast milk to treat and prevent fungal infections. At the very least, the use of human breast milk makes the Larsson composition less economical and difficult to rapidly produce and store. Further, after three days of treatment, the compositions of the present disclosure are shown to significantly decrease the duration of undifferentiated diarrhea in non-neonatal babies and children; where the conditions of the gastrointestinal tract are harsher than in the neonate. This is in contrast to Larsson et al., US 2006/0134101, which provides a method for the use of avian antibodies for treatment and prophylaxis of enteric infections in newborn infants. This is also contrast to, Sarker et al., 2001, who reported a clinical trial of hyperimmunized chicken egg yolk immunoglobulin in non-neonate children with rotavirus diarrhea that showed little or no difference in the duration of diarrhea. (Sarker et al., 2001, Randomized, placebo-controlled, clinical trial of hyperimmunized chicken egg yolk immunoglobulin in children with rotavirus diarrhea. J. Pediatr. Gastroenterol Nutr. 32: 19-25).

In addition, the present compositions utilize dried whole egg containing antigen-specific IgY with a protective and reactive carrier matrix such as bovine colostrum to both (1) protect the antibodies during oral administration, and (2) to further activate passive immunity as described. This is in contrast to Lee et al., US 2003/0185856, which provides a method for the production of egg containing anti-pathogenic bacteria specific IgY and compositions in the form of yogurt or ice cream containing the IgY; however, a protective and reactive carrier matrix is not described. Yogurt and ice cream generally do not have a high enough concentration of the matrix components present in the matrix derived from colostrum.

Unlike an immunoregulatory response, the effects of administration of the composition could generally be observed within 6-12 hours of the first administration. The compositions of the disclosure are effective without reliance on the subject's immune response.

Example 5. Clinical Study—Unexpected Efficacy in Typhoid Fever

Evidence for the efficacy of the claimed composition was provided through an unplanned and unexpected demonstration of clinical efficacy caused by an unknown prior inoculation.

During one field study in India a small number of children were brought forward for treatment who had been clinically diagnosed with "Typhoid Fever". Typhoid fever is an infection most commonly caused by a type of bacteria called *Salmonella typhi* (*S. typhi*). Classical symptoms of this disease, beyond diarrhea, are caused by its systemic infection phase. The bacteria typically first travel into the intestines, and then into the bloodstream, where they can migrate to the lymph nodes, gallbladder, liver, spleen, and other parts of the body. These patients displayed classical symptoms of advanced disease, including high fever, general ill-feeling, and abdominal pain, and significantly, a classical rash— "rose spots," which are small red spots on the abdomen and chest.

As is typical for this practice environment, no diagnostic testing was performed on these patients beyond gross physical examination. Although these patients did not fit into the inclusion criteria for the field study they were provided with the composition of Example 1B, at the request of the attending physicians, on compassionate grounds.

The standard inoculation protocol for chickens with three commercially available vaccines did not specifically include antigens for *Salmonella*, so only a limited clinical response was expected. A mild improvement due to endotoxin neutralization was predicted, with some associated relief of the major diarrheal symptoms, but no effect on the course of the disease itself.

Surprisingly, all of the typhoid fever patients receiving the composition of Example 1B showed dramatic improvement in diarrhea symptoms within 24 to 48 hours. This improvement appeared to be beyond what might be expected for endotoxin neutralization alone. More surprising however was the fact that the systemic symptoms of typhoid fever in all cases also disappeared within the following 24 hour period, yielding a time period to normal or near normal status of 48 to 72 hours. In typhoid fever symptoms usually improve in 2 to 4 weeks with treatment.

None of the patients exhibited any rebound or recurrence of disease during the field trial observation period (5 days). It is well established that symptoms may return rapidly if the treatment has not completely cured the infection.

Treatment with the composition of Example 1B, once per day for three consecutive was sufficient to cause (in conjunction with standard of care) a dramatic reduction in symptoms of the disease, both GI and systemically, within a remarkably short period of time. The timeframe of response could not be explained by natural or "standard of care" effects alone.

In an attempt to discover the source of this unexpected efficacy, the entire history of the production process for that lot was carefully reviewed. It was discovered that as part of an ordinary, but discretionary, inoculation protocol for commercial laying hens the chickens we used were inoculated with *salmonella* vaccine.

Although the birds were vaccinated as chicks, the formulation was found to be highly efficacious against *Salmonella typhi*. *Salmonella* was not one of the antigens in the inoculation protocol used for the chickens in the Example 1 preparations. The unexpected response of these typhoid fever patients to the composition of the disclosure was noted to be very surprising to the attending physicians during the field trial.

Example 6. Quantitative ELISA for Egg Powder Specific IgY and Total IgY

The antibody activity of total IgY and specific anti-antigen IgY can be determined using Enzyme-Linked Immunosorbant Assay (ELISA) by a modification of the method of Liou et al., 2011, J. Anim. Vet. Adv., 10(18): 2349-2356, as described below.

Microtiter plates are coated with either 100 uL mixed antigen preparation (10 ug per well) or coated with 100 uL rabbit anti-chicken IgY antibody (10 ug/mL, Sigma-Aldrich), for control wells. The plate is incubated overnight at 4° C. After washing with PBS-Tween 20 buffer, plates are blocked with 2% BSA and incubated overnight at 4° C. The wells are then washed with PBS-Tween 20 buffer and once with PBS. Thereafter, diluted dried egg powder stock (10 mg/mL) is serially diluted with 1% BSA and added to sample wells at 100 uL per well. Wells for standard curve are filled with 100 uL serial dilutions of standard IgY at, e.g., at concentration ranges of, e.g., 0.015-1 ug/mL and incubated overnight at 4° C. After washing with PBS-Tween 20 buffer, 100 uL of alkaline phosphatase-conjugated goat anti-chicken IgY is added to the wells and incubated 2 hours at 37° C. After washing with PBS-Tween 20 buffer, 100 uL disodium p-nitrophenyl phosphate as substrate is added to each well and allowed to react for 10 min at 37° C. The absorbance is measured at 405 nm using a plate reader. The absorbance of standard curves provides a relative measurement of specific anti-antigen IgY concentration.

For measurement of total IgY, each well of the microtiter plate is coated with rabbit anti-chicken IgY antibody (10 ug/mL). After incubation and washing as above, 100 uL of diluted dried egg powder is added and assay is performed as above.

Although the invention has been described with reference to the above examples, it will be understood that modifications and variations are encompassed within the spirit and scope of the invention. Accordingly, the invention is limited only by the following claims.

What is claimed is:

1. A composition for administration to a non-neonate human in need thereof, the composition comprising:
   a) a non-neonate effective amount of at least one antigen specific antibody, or antigen binding fragment thereof, obtained from a first nonhuman animal; and,
   b) a carrier matrix comprising, consisting of, obtained from, isolated from, or derived from full fat colostrum obtained from a second nonhuman animal, wherein the carrier matrix comprises at least two components selected from the group consisting of enzymes, lactoferrin, transferrin, nonspecific immunoglobulins, cytokines, white blood cells, complement components, interferons, growth factors, and fibronectin,
   wherein the at least one antigen specific antibody or antigen binding fragment thereof and the colostrum are obtained from different non-human animals.

2. The composition of claim 1, wherein the carrier matrix comprises bovine colostrum.

3. The composition of claim 1, wherein the at least two components of the carrier matrix are selected from the group consisting of lysozyme, phospholipase, defensins, opsonins, nonspecific immunoglobulins, proline-rich polypeptides (PRPs), components of the complement system, beta-lysin, lactoferrin, lactoperoxidase, transferrin, cytokines, interleukins, chemokines, interferons, TNF-alpha, fibronectin, leukocytes, white blood cells, phagocytes, macrophages, monocytes, neutrophils, polymorphonuclear cells, dendritic cells, mast cells, eosinophils, basophils, natural killer (NK) cells, lymphokine activated killer (LAK) cells, elastase, cathepsin G, myeloperoxidase, NADPH oxidase, insulin-like growth factor I, insulin-like growth factor II, transforming growth factor alpha, transforming growth factor beta 1, transforming growth factor beta 2, fibroblast growth factors, epidermal growth factor, granulocyte-macrophage stimulating growth factor, platelet-derived growth factor, vascular endothelial growth factor, colony-stimulating factor-I, leptin, hepatocyte growth factor, and combinations thereof.

4. The composition of claim 1, wherein the antigen is derived from a pathogen, a pathogen related toxin, a pathogen related adhesion element, undesirable strain, or a combination thereof.

5. The composition of claim 4, wherein the pathogen is selected from a human or veterinary, enteric or gastrointestinal, pathogen causing gastroenteritis.

6. The composition of claim 4, wherein the pathogen is selected from the group consisting of: *Campylobacter jejuni, Salmonella, Salmonella typhimurium, Salmonella enterica serovar Typhi, Shigella dystenteriae, Plesiomonas shigelloides, Escherichia coli*, enteropathogenic *E. coli*, enterotoxigenic *E. coli*, enteroaggregative *E. coli*, enteroinvasive *E. coli*, haemorrhagic *E. coli, Clostridium difficile, Yersinia enterocolitica, Vibrio cholerae* O1, *Vibrio* O139, Non-O1 *Vibrios, Vibrio parahaemolyticus, Aeromonas hydrophila, Clostridium perfringens*, enterohepatic *Helicobacter, Helicobacter pylori, Staphylococcus aureus, Klebsiella, Gardnerella* spp., *Neisseria gonorrhoeae, Chlamydiaceae trachomatis, Mycoplasma* spp., *Trichomonas vaginalis*, herpes virus type 1, herpes virus type 2, *Candida albicans, Candida glabrata, Candida tropicalis, Candida parapsilosis* and *Candida krusei*, Group A *Streptococcus* spp., rotavirus, coronavirus, norovirus, calicivirus, enteric adenovirus, cytomegalovirus, astrovirus, *S. pneumoniae, H influenzae, Neisseria gonorrhoeae*, herpes zoster virus, *Fusarium* spp., and *Acanthamoeba* spp.

7. The composition of claim 4, wherein the at least one antigen specific antibody, or antigen binding fragment thereof, comprise a mixture of polyclonal antibodies specific for a pathogen, a pathogen related toxin, or a pathogen related adhesion element, derived from one, two, three, four, five, six, seven, or eight, or more, of different pathogenic microorganisms.

8. The composition of claim 4, wherein the pathogen related toxin comprises an endotoxin or exotoxin.

9. The composition of claim 4, wherein the pathogen related adhesion element comprises adhesins, cadherins, cilia, fimbrillae, a viral adhesion structure, or a combination thereof.

10. The composition of claim 1, wherein the at least one antibody is selected from a polyclonal antibody or a monoclonal antibody.

11. The composition of claim 10, wherein the at least one antibody is an IgG.

12. The composition of claim 10, wherein the at least one antibody is IgY.

13. The composition of claim 10, wherein the at least one antibody is a polyclonal antibody.

14. The composition of claim 2, wherein the colostrum is powderized full fat bovine colostrum.

15. The composition of claim 14, wherein the colostrum is non-hyperimmune bovine colostrum.

16. The composition of claim 1, wherein the composition is in a solid form or a liquid form.

17. The composition of claim 1, wherein the composition is in a solid form.

18. The composition of claim 1, further comprising a pharmaceutically acceptable diluent, binder, excipient, lubricant, sweetening agent, flavoring agent, wetting agent, or absorbent.

19. A method for preparing the composition of claim 1, comprising:
    (a) obtaining a solid form of the at least one antigen specific antibody, or antigen binding fragment thereof, that had been derived from a first nonhuman animal;
    (b) obtaining a solid form of the at least one carrier matrix, comprising, consisting of, obtained from, isolated from, or derived from full fat colostrum that had been derived from a second nonhuman animal, wherein the carrier matrix comprises at least two components selected from the group consisting of enzymes, lactoferrin, transferrin, nonspecific immunoglobulins, cytokines, white blood cells, complement components, interferons, growth factors, and fibronectin wherein the at least one antigen specific antibody or antigen binding fragment thereof and the colostrum each had been derived from different nonhuman animals; and
    (c) mixing the carrier matrix with the antigen specific antibody or antigen binding fragment thereof.

20. The method of claim 19, wherein the matrix comprises bovine colostrum.

21. The method of claim 19, wherein the at least two components of the carrier matrix are selected from the group consisting of lysozyme, phospholipase, defensins, opsonins, nonspecific immunoglobulins, proline-rich polypeptides (PRPs), components of the complement system, beta-lysin, lactoferrin, lactoperoxidase, transferrin, cytokines, interleukins, chemokines, interferons, TNF-alpha, fibronectin, leukocytes, white blood cells, phagocytes, macrophages, monocytes, neutrophils, polymorphonuclear cells, dendritic cells, mast cells, eosinophils, basophils, natural killer (NK) cells, lymphokine activated killer (LAK) cells, elastase, cathepsin G, myeloperoxidase, NADPH oxidase, insulin-like growth factor I, insulin-like growth factor II, transforming growth factor alpha, transforming growth factor beta 1, transforming growth factor beta 2, fibroblast growth factors, epidermal growth factor, granulocyte-macrophage stimulating growth factor, platelet-derived growth factor, vascular endothelial growth factor, colony-stimulating factor-I, leptin, hepatocyte growth factor, and combinations thereof.

22. A method for the treatment or prevention of a pathogenic infection or undesirable strain of microorganisms in a non-neonate human in need thereof; the method comprising administration of a composition comprising:
a) a non-neonate effective amount of at least one antigen specific antibody, or antigen binding fragment thereof, obtained from a first nonhuman animal; and,
b) a carrier matrix comprising, consisting of, obtained from, isolated from, or derived from full fat colostrum obtained from a second nonhuman animal, wherein the carrier matrix comprises at least two components selected from the group consisting of enzymes, lactoferrin, transferrin, nonspecific immunoglobulins, cytokines, white blood cells, complement components, interferons, growth factors, and fibronectin,
wherein the at least one specific binding molecule and the colostrum of the carrier matrix are obtained from different non-human animals.

23. The method of claim 22, wherein the pathogenic infection is selected from the group consisting of undifferentiated diarrhea, traveler's diarrhea, rotavirus diarrhea, toxin-mediated diarrhea, cholera, *C. difficile* infection, dysentery, typhoid fever, and peptic ulcers.

24. The method of claim 23, wherein the undifferentiated diarrhea is pediatric undifferentiated diarrhea.

25. The method of claim 22, wherein the composition is administered in an amount effective for conferring passive immunity to a subject.

26. The method of claim 22, wherein the treatment or prevention of an undesirable strain of microorganisms is used for gastrointestinal flora management.

27. The composition of claim 1 useful as a nutritional composition for administering to the non-neonate human subject in need thereof, wherein the subject is afflicted with a disease that creates special dietary needs wherein the disease is selected from the group consisting of undifferentiated diarrhea, pediatric diarrhea, Crohn's disease, and ulcerative colitis.

28. The method of claim 20, wherein the bovine colostrum is powderized full fat bovine colostrum.

29. The method of claim 28, wherein the bovine colostrum is non-hyperimmune bovine colostrum.

30. The composition of claim 3, wherein the carrier matrix comprises a growth factor and an antimicrobial factor.

31. The composition of claim 3, wherein the carrier matrix comprises three or more non-immunoglobulin components of colostrum.

32. The composition of claim 31, wherein the carrier matrix comprises four or more non-immunoglobulin components of colostrum.

33. The composition of claim 32, wherein the carrier matrix comprises five or more non-immunoglobulin components of colostrum.

34. The composition of claim 7, wherein the different pathogenic microorganisms comprise *E. coli*, rotavirus, and corona virus.

35. The composition of claim 7, wherein the mixture of polyclonal antibodies comprise IgY antibodies specific for at least enterotoxigenic *E. coli* spp., *E. coli* K99 pili adherence factor, *Clostridium perfringens* toxoid, *Salmonella typhimurium*, rotavirus, and coronavirus.

36. The method of claim 22, wherein the matrix comprises bovine colostrum.

37. The method of claim 36, wherein the bovine colostrum is powderized full fat bovine colostrum.

38. The method of claim 37, wherein the colostrum is non-hyperimmune bovine colostrum.

39. The method of claim 22, wherein the at least two components of the carrier matrix are selected from the group consisting of lysozyme, phospholipase, defensins, opsonins, nonspecific immunoglobulins, proline-rich polypeptides (PRPs), components of the complement system, beta-lysin, lactoferrin, lactoperoxidase, transferrin, cytokines, interleukins, chemokines, interferons, TNF-alpha, fibronectin, leukocytes, white blood cells, phagocytes, macrophages, monocytes, neutrophils, polymorphonuclear cells, dendritic cells, mast cells, eosinophils, basophils, natural killer (NK) cells, lymphokine activated killer (LAK) cells, elastase, cathepsin G, myeloperoxidase, NADPH oxidase, insulin-like growth factor I, insulin-like growth factor II, transforming growth factor alpha, transforming growth factor beta 1, transforming growth factor beta 2, fibroblast growth factors, epidermal growth factor, granulocyte-macrophage stimulating growth factor, platelet-derived growth factor, vascular endothelial growth factor, colony-stimulating factor-I, leptin, hepatocyte growth factor, and combinations thereof.

40. The method of claim 39, wherein the at least two components of the carrier matrix include a growth factor and an antimicrobial factor.

41. The method of claim 40, wherein the carrier matrix comprises three or more non-immunoglobulin components of colostrum.

42. The method of claim 41, wherein the carrier matrix comprises four or more non-immunoglobulin components of colostrum.

43. The method of claim 42, wherein the carrier matrix comprises five or more non-immunoglobulin components of colostrum.

44. The method of claim 43, wherein the pathogen is selected from the group consisting of: *Campylobacter jejuni*, *Salmonella*, *Salmonella typhimurium*, *Salmonella enterica* serovar *Typhi*, *Shigella* dystenteriae, *Plesiomonas shigelloides*, *Escherichia coli*, enteropathogenic *E. coli*, enterotoxigenic *E. coli*, enteroaggregative *E. coli*, enteroinvasive *E. coli*, haemorrhagic *E. coli*, *Clostridium difficile*, *Yersinia enterocolitica*, *Vibrio cholerae* O1, *Vibrio* O139, Non-O1 Vibrios, *Vibrio parahaemolyticus*, *Aeromonas hydrophila*, *Clostridium perfringens*, enterohepatic *Helicobacter*, *Helicobacter pylori*, *Staphylococcus aureus*, *Klebsiella*, *Gardnerella* spp., *Neisseria gonorrhoeae*, *Chlamydiaceae trachomatis*, *Mycoplasma* spp., *Trichomonas vaginalis*, herpes virus type 1, herpes virus type 2, *Candida albicans*, *Candida glabrata*, *Candida tropicalis*, *Candida parapsilosis* and *Candida krusei*, Group A *Streptococcus* spp., rotavirus, coronavirus, norovirus, calicivirus, enteric adenovirus, cytomegalovirus, astrovirus, *S. pneumoniae*, *H. influenzae*, *Neisseria gonorrhoeae*, herpes zoster virus, *Fusarium* spp., and *Acanthamoeba* spp.

45. The method of claim 22, wherein the antigen is derived from a pathogen, a pathogen related toxin, a pathogen related adhesion element, undesirable strain, or a combination thereof.

46. The method of claim 45, wherein the pathogen is selected from a human or veterinary, enteric or gastrointestinal, pathogen causing gastroenteritis.

47. The method of claim 44, wherein the at least one antigen specific antibody, or antigen binding fragment thereof, comprise a mixture of polyclonal antibodies specific for a pathogen, a pathogen related toxin, or a pathogen related adhesion element, derived from one, two, three, four, five, six, seven, or eight, or more, of different pathogenic microorganisms.

48. The method of claim 47, wherein the different pathogenic microorganisms comprise *E. coli*, rotavirus, and corona virus.

49. The method of claim 47, wherein the mixture of antibodies comprise IgY antibodies specific for at least enterotoxigenic *E. coli* spp., *E. coli* K99 pili adherence factor, *Clostridium perfringens* toxoid, *Salmonella typhimurium*, rotavirus, and coronavirus.

50. The composition of claim 1, wherein one dose of the composition comprises 1 g to 7 g dried immune egg and 1 g to 7 g dried full fat bovine colostrum.

\* \* \* \* \*